United States Patent
Dubois et al.

(10) Patent No.: US 7,345,198 B2
(45) Date of Patent: *Mar. 18, 2008

(54) METHOD FOR THE PRODUCTION OF ACRYLIC ACID FROM PROPANE, IN THE PRESENCE OF MOLECULAR OXYGEN

(75) Inventors: Jean-Luc Dubois, Millery (FR);
Fabienne Desdevises, Millery (FR);
Stéphanie Serreau, Oullins (FR);
Damien Vitry, Richebourg (FR);
Wataru Ueda, Tokyo (JP)

(73) Assignee: Arkema, Puteaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/526,877

(22) PCT Filed: Sep. 9, 2003

(86) PCT No.: PCT/FR03/02674

§ 371 (c)(1),
(2), (4) Date: Sep. 6, 2005

(87) PCT Pub. No.: WO2004/024666

PCT Pub. Date: Mar. 25, 2004

(65) Prior Publication Data

US 2006/0128989 A1     Jun. 15, 2006

(30) Foreign Application Priority Data

Sep. 10, 2002  (FR) ............................ 02 11197
May 27, 2003  (FR) ............................ 03 06412

(51) Int. Cl.
*C07C 51/16*  (2006.01)

(52) U.S. Cl. ............................................... 562/549

(58) Field of Classification Search .............. 562/523, 562/542, 549, 598, 599
See application file for complete search history.

(56) References Cited

U.S. PATENT DOCUMENTS

| 5,380,933 | A | 1/1995 | Ushikubo et al. | |
| 6,867,328 | B2* | 3/2005 | Borgmeier et al. | 562/598 |
| 2003/0017944 | A1 | 1/2003 | Hinago et al. | |
| 2003/0088124 | A1* | 5/2003 | Dubois | 562/547 |
| 2005/0054880 | A1* | 3/2005 | Dubois et al. | 562/547 |

FOREIGN PATENT DOCUMENTS

| DE | 101 45 958 A1 | 5/2002 |
| EP | 1 238 960 A1 | 9/2002 |
| FR | 2 833 005 A1 | 6/2003 |
| JP | 2000-256257 A | 9/2000 |

OTHER PUBLICATIONS

Preliminary Search Report for French Application No. 03/06412, dated Feb. 20, 2004.
International Search Report for PCT/FR03/02674, dated Apr. 3, 2004.

* cited by examiner

*Primary Examiner*—Karl Puttlitz
(74) *Attorney, Agent, or Firm*—Buchanan Ingersoll & Rooney PC

(57) ABSTRACT

The invention concerns the production of acrylic acid from propane in the presence of molecular oxygen. Said method consists in passing a gas mixture comprising propane, molecular oxygen, water vapour and, optionally, an inert gas, on a catalyst of formula (I) $Mo_1V_aTe_bNb_cSi_dO_x$ to oxidize propane into acrylic acid, the propane/molecular oxygen mol ratio in the initial gas mixture being not less than 0.5.

36 Claims, 1 Drawing Sheet

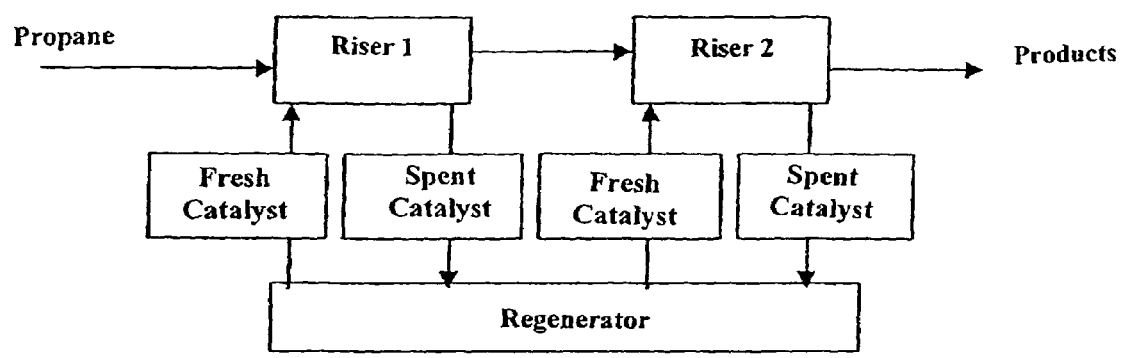
Single figure

METHOD FOR THE PRODUCTION OF ACRYLIC ACID FROM PROPANE, IN THE PRESENCE OF MOLECULAR OXYGEN

The present invention relates to the production of acrylic acid from propane in the presence of molecular oxygen.

It is known from European patent application No. EP-A-608838 to prepare an unsaturated carboxylic acid from an alkane according to a catalytic oxidation reaction in vapour phase in the presence of a catalyst containing a mixed metal oxide comprising as essential components, Mo, V, Te, O, as well as at least one element chosen from the group constituted by niobium, tantalum, tungsten, titanium, aluminium, zirconium, chromium, manganese, iron, ruthenium, cobalt, rhodium, nickel, palladium, platinum, antimony, bismuth, boron, indium and cerium, these elements being present in very precise proportions. The reaction can be implemented using a gaseous mixture composed of the alkane, oxygen, an inert gas and water vapour corresponding to the following molar proportions: alkane/oxygen/inert gas/water vapour=1/0.1-10/0-20/0.2-70 and preferably 1/1-5/0-10/5-40.

Moreover, the European patent application No. EP-A-895809 describes catalysts based on oxides comprising molybdenum, vanadium, niobium, oxygen, tellurium and/or antimony, as well as at least one other element such as iron or aluminium. These catalysts can be used for the conversion of propane to acrylic acid, in the presence of molecular oxygen, as illustrated in Examples 9 and 10. Example 9, in particular, describes the oxidation of propane using a catalyst of formula $Mo_1V_{0.33}Nb_{0.11}Te_{0.22}O_n$ from a gas flow composed of propane, oxygen, helium and a flow of water vapour, according to a molar ratio propane/oxygen/helium/water vapour of approximately 1/3.2/12.1/14.3. In such a gas flow, the flow of reactive gas has a very low concentration of propane. Consequently the recycling of the unconverted propane is much more difficult because this unconverted propane is too diluted in the reaction flow.

The aim of the invention is to propose a method for the production of acrylic acid from propane, in the presence of molecular oxygen, which allows a higher conversion of propane to be obtained while retaining good acrylic acid selectivity.

The inventors have discovered that this aim can be achieved by passing a gaseous mixture of propane, oxygen and water vapour, and if appropriate an inert gas, over a particular catalyst, under conditions such that the oxygen of the gaseous mixture is in a substoichiometric proportion in relation to the propane introduced, which probably allows the catalyst to act in a similar way to a redox system and provides the oxygen which is lacking so that the reaction is carried out in a satisfactory way.

The advantages of this novel method are the following:
the limitation of the overoxidation of the products formed which takes place in the presence of too great a quantity of molecular oxygen; according to the present invention, due to the fact of operating in substoichiometry, the formation of $CO_X$ (carbon monoxide and carbon dioxide), degradation products, is reduced, which allows the acrylic acid selectivity to be increased;
the acrylic acid selectivity is maintained at a good level;
the conversion is increased without loss of selectivity;
the catalyst undergoes only a low reduction and therefore a small loss of its activity; it can easily be regenerated by heating in the presence of oxygen or a gas containing oxygen after a certain period of use; after regeneration, the catalyst regains its initial activity and can be used in another reaction cycle;

moreover, the separation of the stages of reduction of the catalyst and of regeneration of the latter can be provided which allows the partial pressure of propane to be increased, such a partial supply pressure of propane being little limited by the existence of an explosive zone created by the propane+oxygen mixture, because the later is present in molecular form in substoichiometric proportions;

moreover, this method allows reduction of the formation of products produced by hydration, in particular propionic acid, acetone and acetic acid.

The subject of the present invention is therefore a method for the production of acrylic acid from propane, in which a gaseous mixture containing propane, molecular oxygen, water vapour as well as, if appropriate, an inert gas, is passed over a catalyst of formula (I):

$$Mo_1V_aTe_bNb_cSi_dO_x \qquad (I)$$

in which:
a is comprised between 0.006 and 1, inclusive;
b is comprised between 0.006 and 1, inclusive;
c is comprised between 0.006 and 1, inclusive;
d is comprised between 0 and 3.5, inclusive; and
x is the quantity of oxygen bound to the other elements and depends on their oxidation state.

in order to oxidize the propane to acrylic acid, this method being characterized in that the molar ratio propane/molecular oxygen in the initial gaseous mixture is greater than or equal to 0.5.

Such a method allows an acrylic acid selectivity to be obtained of close to 60% and a high conversion of propane. Moreover, it can easily be implemented in a fluidized bed or in a moving bed and the injection of the reagents can be carried out at different points of the reactor, so as to be outside of the flammability zone while having a high propane concentration and, consequently, a high catalyst productivity.

According to a particularly advantageous embodiment, the method according to the invention comprises the following stages:
a) the gaseous mixture is introduced into a first reactor with a moving catalyst bed,
b) at the outlet of the first reactor, the gases are separated from the catalyst;
c) the catalyst is returned into a regenerator;
d) the gases are introduced into a second reactor with a moving catalyst bed;
e) at the outlet of the second reactor, the gases are separated from the catalyst and the acrylic acid contained in the separated gases is recovered;
f) the catalyst is returned into the regenerator; and
g) the regenerated catalyst from the regenerator is reintroduced into the first and second reactors;

According to another advantageous embodiment of the invention, the reactor or reactors are also provided with a cocatalyst. The above stages can be carried out in a similar way using a catalyst and a cocatalyst.

According to another advantageous embodiment of the invention, the method comprises the repetition, in a reactor provided with the catalyst of formula (I) and, if appropriate, with a cocatalyst, of the cycle comprising the following successive stages:
1) a stage of injection of the gaseous mixture as defined above;
2) a stage of injection of water vapour and, if appropriate of inert gas;

3) a stage of injection of a mixture of molecular oxygen, water vapour and, if appropriate, inert gas; and
4) a stage of injection of water vapour and, if appropriate inert gas.

According to an improvement of the advantageous embodiment which has just been described, the cycle comprises an additional stage which precedes or follows stage 1) and during which a gaseous mixture corresponding to that of stage 1) is injected but without the molecular oxygen, the molar ratio propane/molecular oxygen then being calculated globally for stage 1) and this additional stage.

According to an advantageous embodiment of the improvement which has just been presented, the additional stage precedes stage 1) in the cycle.

Other characteristics and advantages of the invention will now be described in detail in the following description which is given with reference to the single attached FIGURE which diagrammatically represents an apparatus which is suitable for the implementation of an advantageous embodiment of the method according to the invention.

DETAILED DESCRIPTION OF THE INVENTION

According to the invention, because the molar ratio propane/molecular oxygen in the initial gaseous mixture is greater than 0.5, the conversion of the propane to acrylic acid using the catalyst is carried out by oxidation, probably according to the following concurrent reactions (1) and (2):

the standard catalytic reaction (1):

$$CH_3-CH_2-CH_3 + 2O_2 \rightarrow CH_2=CH-COOH + 2H_2O \quad (1)$$

and the redox reaction (2):

$$SOLID_{oxidized} + CH_3-CH_2-CH_3 \rightarrow SOLID_{reduced} + CH_2=CH-COOH \quad (2)$$

The propane/water vapour volume ratio in the initial gaseous mixture is not critical and can vary within wide limits.

Similarly, the proportion of inert gas, which can be helium, krypton, a mixture of these two gasses, or nitrogen, carbon dioxide, etc., is also not critical and can also vary within wide limits.

The proportions of the constituents of the initial gaseous mixture are generally as follows (in molar ratios):

propane/oxygen/inert(He—Kr)/H$_2$O (vapour)=1/0.05-2/1-10/1-10

Preferably, they are 1/0.1-1/1-5/1-5.

Yet more preferably, they are 1/0.167-0.667/2-5/2-5. As particularly beneficial proportions the following may also be cited:

1/0.2-0.4/4-5/4-5.

Generally, reactions (1) and (2) are carried out at a temperature of 200 to 500° C., preferably from 250 to 450° C., yet more preferably from 350 to 400° C.

The pressure in the reactor or reactors is generally from $1.01 \times 10^4$ to $1.0 \times 10^6$ Pa (0.1 to 10 atmospheres), preferably from $5.05 \times 10^4$ to $5.05 \times 10^5$ Pa (0.5-5 atmospheres).

The residence time in the reactor, or if there are several, in each reactor, is generally from 0.01 to 90 seconds, preferably from 0.1 to 30 seconds.

The catalyst corresponds to the formula (I):

$$Mo_1V_aTe_bNb_cSi_dO_x \quad (I)$$

in which:
a is comprised between 0.006 and 1, inclusive;
b is comprised between 0.006 and 1, inclusive;
c is comprised between 0.006 and 1, inclusive;
d is comprised between 0 and 3.5, inclusive; and
x is the quantity of oxygen bound to the other elements and depends on their oxidation state.

Advantageously:
a is comprised between 0.09 and 0.8, inclusive;
b is comprised between 0.04 and 0.6, inclusive;
c is comprised between 0.01 and 0.4, inclusive; and
d is comprised between 0.4 and 1.6, inclusive.

The oxides of the different metals included in the composition of the catalyst of formula (I) can be used as raw materials in the preparation of this catalyst, but the raw materials are not limited to the oxides; as other raw materials, there may be mentioned:

in the case of molybdenum, ammonium molybdate, ammonium paramolybdate, ammonium heptamolybdate, molybdic acid, molybdenum halides or oxyhalides such as MoCl$_5$, organometallic compounds of molybdenum such as molybdenum alkoxides such as Mo(OC$_2$H$_5$)$_5$, acetylacetone molybdenyl;

in the case of vanadium, ammonium metavanadate, vanadium halides or oxyhalides such as VCl$_4$, VCl$_5$ or VOCl$_3$, organometallic compounds of vanadium such as vanadium alkoxides such as VO(OC$_2$H$_5$)$_3$;

in the case of tellurium, tellurium, telluric acid and TeO$_2$;

in the case of niobium, niobic acid, niobium tartrate, niobium hydrogen oxalate, oxotrioxalatoammonium niobate {(NH$_4$)$_3$[NbO(C$_2$O$_4$)$_3$]·1.5H$_2$O}, niobium and ammonium oxalate, niobium oxalate and tartrate, nobium halides or oxyhalides such as NbCl$_3$, NbCl$_5$ and organometallic compounds of niobium such as niobium alkoxides such as Nb(OC$_2$H$_5$)$_5$, Nb(O-n-Bu)$_5$;

and, generally, all the compounds which are able to form an oxide by calcination, namely, the metallic salts of organic acids, the metallic salts of mineral acids, the metal complex compounds, etc.

The source of silicon is generally constituted by colloidal silica and/or polysilicic acid.

According to particular embodiments, the catalyst of formula (I) can be prepared by mixing aqueous solutions of niobic acid, ammonium heptamolybdate, ammonium metavanadate, telluric acid under stirring, by the addition preferably of colloidal silica, then by precalcinating under air between 280 and 340° C., preferably at approximately 320° C. and by calcinating under nitrogen at approximately 600° C.

Preferably, in the catalyst of formula (I):
a is comprised between 0.09 and 0.8, inclusive;
b is comprised between 0.04 and 0.6, inclusive;
c is comprised between 0.01 and 0.4, inclusive; and
d is comprised between 0.4 and 1.6, inclusive.

Preferred Method for the Preparation of the Catalyst of Formula (I)

The catalyst of formula (I) can be prepared using a method in which:
1) a solution of niobium is prepared by mixing oxalic acid and niobic acid, then optionally separation with a view to recovering the solute;
2) a solution of molybdenum, vanadium and tellurium is prepared;
3) the two preceding solutions are coprecipitated by adding a silica solution;

4) the precipitate is dried, which produces a precursor with the formula:

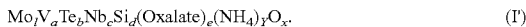
$$Mo_jV_aTe_bNb_cSi_d(Oxalate)_e(NH_4)_yO_x. \quad (I')$$

in which a, b, c, d and x are defined as previously and e is comprised between 0.006 and 3.5, inclusive;

y is comprised between 0.006 and 3.5, inclusive;

5) the precursor is precalcinated; then
6) the precursor is calcinated.

The separation of stage 1) can be carried out by centrifugation, decantation or filtration.

The drying of stage 4) can be carried out in an oven in a thin layer, by atomization, freeze-drying, zeodration, with micro waves etc.

The precalcination can be carried out under air flow at 270-300° C. or under static air at 320° C., in a fluidized bed, in a rotary tube, in a so-called aerated fixed bed, so that the catalyst pellets are separated from each other in order to prevent them from fusing during precalcination or possibly during calcination.

The calcination is preferably carried out under very pure nitrogen and at a temperature less than 600° C., for example in a rotary furnace, in a fixed bed, in a fluidized bed and for a duration which can be 2 hours.

The catalyst obtained at the end of the calcination can be ground in order to produce smaller particles. If the grinding is continued until a powder constituted by particles of approximately the size of a micron is obtained, the powder can subsequently be returned to its form using a binding agent such as for example silica in the form of polysilicic acid, the suspension then being dried again, for example by atomization.

According to a particularly preferred embodiment, the precalcination is carried out either at a temperature of approximately 275° C. under an air flow of at least 10 ml/min/g of catalyst;

or at a temperature ranging from 300 to 350° C. under an air flow less than 10 ml/min/g of catalyst.

According to a most particularly preferred embodiment, the precalcination is carried out at approximately 320° C. under no air flow.

Regeneration of the Catalyst

During the redox reaction (2), the catalyst undergoes reduction and a progressive loss of its activity. This is why, once the catalyst has at least partially changed to the reduced state, its regeneration is carried out according to reaction (3):

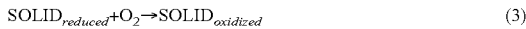
$$SOLID_{reduced} + O_2 \rightarrow SOLID_{oxidized} \quad (3)$$

by heating in the presence of oxygen or a gas containing oxygen at a temperature of 250 to 500° C., for a time necessary for the reoxidation of the catalyst.

The proportions of the constituents of the regeneration gaseous mixture are generally as follows (in molar ratios):

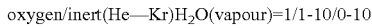
$$\text{oxygen/inert(He—Kr)}H_2O(\text{vapour}) = 1/1\text{-}10/0\text{-}10$$

Preferably, they are 1/1-5/0-5.

Instead of using the oxygen alone, dry air (21% $O_2$) can be used. Instead of or in addition to the water vapour, moist air can thus be used.

Generally the method is carried out until the reduction ratio of the catalyst is comprised between 0.1 and 10 g of oxygen per kg of catalyst.

This reduction ratio can be monitored during the reaction through the quantity of products obtained. Then the equivalent quantity of oxygen is calculated. It can also be monitored through the exothermicity of the reaction. The reduction ratio can also be monitored through the quantity of oxygen consumed in the regenerator.

After regeneration, which can be carried out under temperature and pressure conditions which are identical to, or different from those of the reactions (1) and (2), the catalyst regains an initial activity and can be reintroduced into the reactors.

The reactions (1) and (2) and the regeneration (3) can be carried out in a standard reactor, such as a fixed bed reactor, a fluidized bed reactor or a moving bed reactor.

Thus the reactions (1) and (2) and the regeneration (3) can be carried out in a device with two stages, namely a reactor and a regenerator which operate simultaneously and in which two catalyst loadings alternate periodically.

The reactions (1) and (2) and the regeneration (3) can also be carried out in the same reactor by alternating the periods of reaction and regeneration.

Preferably, the reactions (1) and (2) and the regeneration (3) are carried out in a reactor with a moving catalyst bed, in particular in a vertical reactor, the catalyst then preferably moving from the bottom upwards.

A operating method with only one passage of the gas or with recycling of the gas can be used.

According to a preferred embodiment, the propylene produced and/or the propane which has not reacted are recycled (or returned) to the inlet of the reactor, i.e. they are reintroduced at the inlet of the reactor, in a mixture or in parallel with the initial mixture of propane, water vapour and if appropriate inert gas or gases.

Use of an Apparatus with Two Reactors and a Regenerator

According to an advantageous embodiment of the invention, the method according to the invention is used in an apparatus such as the one represented in the attached FIGURE.

The initial gaseous mixture comprising propane, molecular oxygen, water vapour as well as, if appropriate, an inert gas, is introduced into a first reactor (Riser 1) containing the moving catalyst bed.

Then, at the outlet of the first reactor, the effluents are separated into gases and the moving bed catalyst.

The catalyst is sent into a regenerator.

The gases are introduced into a second reactor (Riser 2) also containing a moving catalyst bed.

At the outlet of the second reactor, the effluents are separated into gases and the moving bed catalyst.

The catalyst is sent into a regenerator.

The gases are treated in a known way, generally by absorption and purification, with a view to recovering the acrylic acid produced.

The regenerated catalyst is reintroduced into the first reactor as well as into the second reactor.

The method thus operates continuously, the circulation of the catalyst between the reactors and the regenerator is carried out in a regular and generally continuous way.

Of course, the single regenerator can be replaced by two or more regenerators.

Moreover, it is possible to add, after the second reactor, other reactors which also have a catalyst circulating between each of these reactors and the regenerator or other regenerators.

Preferably, the first and second reactors are vertical and the catalyst is transported upwards by the gas flow.

A method of operating with only one passage of gases or with recycling of the products leaving the second reactor can be used.

According to a preferred embodiment of the invention, after treatment of the gas originating from the second reactor, the propylene produced and/or the propane which has not reacted are recycled (or returned) to the inlet of the reactor, i.e. they are reintroduced at the inlet of the first reactor, in a mixture or in parallel with the initial mixture of propane, oxygen, water vapour and if appropriate of inert gas or gases.

Use of a Cocatalyst

According to another advantageous embodiment of the invention, the gaseous mixture also passes over a cocatalyst.

This has the advantage of reducing the production of propionic acid, which is generally a by-product of the conversion reaction and which poses problems in certain applications of acrylic acid when it is present in too great a quantity.

Thus, the propionic acid/acrylic acid ratio is greatly reduced at the outlet of the reactor.

Moreover, the formation of acetone, which is also a by-product of the production of acrylic acid from propane, is reduced.

To this end, at least one of the reactors comprises a cocatalyst with the following formula (II):

$$Mo_l Bi_{a'} Fe_{b'} Co_{c'} Ni_{d'} K_{e'} Sb_{f'} Ti_{g'} Si_{h'} Ca_{i'} Nb_{j'} Te_{k'} Pb_{l'} W_{m'} Cu_{n'} \quad (II)$$

in which:
- a' is comprised between 0.006 and 1, inclusive;
- b' is comprised between 0 and 3.5, inclusive;
- c' is comprised between 0 and 3.5, inclusive;
- d' is comprised between 0 and 3.5, inclusive;
- e' is comprised between 0 and 1, inclusive;
- f' is comprised between 0 and 1, inclusive;
- g' is comprised between 0 and 1, inclusive;
- h' is comprised between 0 and 3.5, inclusive;
- i' is comprised between 0 and 1, inclusive;
- j' is comprised between 0 and 1, inclusive;
- k' is comprised between 0 and 1, inclusive;
- l' is comprised between 0 and 1, inclusive;
- m' is comprised between 0 and 1, inclusive; and
- n' is comprised between 0 and 1, inclusive.

Such a cocatalyst can be prepared in the same way as the catalyst of formula (I).

The oxides of the different metals included in the composition of the cocatalyst of formula (II) can be used as raw materials in the preparation of this cocatalyst, but the raw materials are not limited to the oxides; as other raw materials, the corresponding nitrates can be mentioned in the case of nickel, cobalt, bismuth, iron or potassium.

Generally, the cocatalyst is present in the form of a moving bed and preferably it is regenerated and circulates, if appropriate, in the same way as the catalyst.

Preferably, in the cocatalyst of formula (II):
- a' is comprised between 0.01 and 0.4, inclusive;
- b' is comprised between 0.2 and 1.6, inclusive;
- c' is comprised between 0.3 and 1.6, inclusive;
- d' is comprised between 0.1 and 0.6, inclusive;
- e' is comprised between 0.006 and 0.01, inclusive.
- f' is comprised between 0 and 0.4, inclusive;
- g' is comprised between 0 and 0.4, inclusive;
- h' is comprised between 0.01 and 1.6, inclusive;
- i' is comprised between 0 and 0.4, inclusive;
- j' is comprised between 0 and 0.4, inclusive;
- k' is comprised between 0 and 0.4, inclusive;
- l' is comprised between 0 and 0.4, inclusive;
- m' is comprised between 0 and 0.4, inclusive; and
- n' is comprised between 0 and 0.4, inclusive.

The weight ratio of the catalyst to the cocatalyst is generally greater than 0.5 and preferably at least 1.

Advantageously, the cocatalyst is present in the two reactors.

The catalyst and the cocatalyst are present in the form of solid catalytic compositions.

They can each be in the form of pellets, generally of 20 to 300 μm in diameter, the catalyst and cocatalyst pellets generally being mixed before implementation of the method according to the invention.

The catalyst and the cocatalyst can also be present in the form of a solid catalytic composition composed of pellets each of which comprises both the catalyst and the cocatalyst.

EXAMPLES

The following examples illustrate the present invention without limiting its scope.

In the formulae given in Example 1, x is the quantity of oxygen bound to the other elements and depends on their oxidation states.

The conversions, selectivities and yields are defined as follows:

Conversion (%) of the propane =

$$\frac{\text{Number of moles of propane having reacted}}{\text{Number of moles of propane introduced}} \times 100$$

Selectivity (%) for acrylic acid =

$$\frac{\text{Number of moles of acrylic acid formed}}{\text{Number of moles of propane having reacted}} \times 100$$

Yield (%) of acrylic acid =

$$\frac{\text{Number of moles of acrylic acid formed}}{\text{Number of moles of propane introduced}} \times 100$$

The selectivities and yields relating to the other compounds are calculated in a similar way.

The conversion ratio is the weight of catalyst (in kg) required to convert 1 kg of propane.

Example 1

Preparation of the Catalyst of Formula
$Mo_l V_{0.33} Nb_{0.11} Te_{0.22} Si_{0.95} O_x$ a) Preparation of a Solution of Niobium 640 g of distilled water then 51.2 g of niobic acid (i.e. 0.304 moles of niobium) are introduced into a 5 l beaker. Then 103.2 g (0.816 moles) of dehydrated oxalic acid is added.

The molar ratio oxalic acid/niobium is therefore 2.69.

The solution obtained previously is heated at 60° C. for 2 hours, being covered so as to avoid evaporation and with stirring. Thus a white suspension is obtained which is left to cool to 30° C. under stirring, which takes approximately 2 hours.

b) Preparation of a Solution of Mo, V and Te 2120 g of distilled water, 488 g of ammonium heptamolybdate (i.e. 2.768 moles of molybdenum), 106.4 g of ammonium metavanadate $NH_4VO_3$ (i.e. 0.912 moles of vanadium) and 139.2 g of telluric acid (supplier: FLUKA) (i.e. 0.608 moles of tellurium) are introduced into a 5 l beaker.

The solution obtained previously is heated at 60° C. for 1 hour and 20 minutes, being covered so as to avoid evaporation and with stirring. In this way a clear red solution is obtained which is left to cool to 30° C. under stirring, which takes approximately 2 hours.

c) Introduction of the Silica 393.6 g of Ludox silica (containing 40% by weight of silica, supplied by Dupont) is introduced under stirring into the previously prepared solution of Mo, V and Te. The latter retains its limpidity and its red colouring.

Then the previously prepared solution of niobium is added. In this way a fluorescent orange gel is obtained after stirring for a few minutes. This solution is then dried by atomization. The atomizer used is a laboratory atomizer (ATSELAB from Sodeva). The atomization takes place in a nitrogen atmosphere.

The working parameters are globally:

flow rate of nitrogen of the order of 45 $Nm^3/h$;

flow rate of slurry of the order of 500 g/h;

inlet temperature of the gas comprised between 155° C. and 170° C.;

outlet temperature of the gas comprised between 92° C. and 100° C.

Then the product recovered (355.2 g), which has a particle size less than 40 microns, is placed in an oven overnight at 130° C., in a teflon-covered plate.

In this way 331 g of dry product is obtained.

d) Calcination

The precalcinations and calcinations were carried out under air and nitrogen flow in steel capacitors. These capacitors are directly installed in muffle furnaces and the air is supplied via the flue. An internal thermometer well allows precise monitoring of the temperature. The cover is useful to prevent air returning towards the catalyst.

Firstly, the 331 g of precursor obtained previously are precalcinated for 4 hours at 300° C. under air flow of 47.9 ml/min/g of precursor.

The solid obtained is then calcinated for 2 hours at 600° C. under a nitrogen flow of 12.8 ml/min/g of solid.

In this way the desired catalyst is obtained.

Example 2

Catalyst Tests a) Apparatus

In order to simulate the method according to the invention, simulations were carried out in a laboratory fixed bed reactor, by generating propane pulses and oxygen pulses.

The following are loaded from the bottom to the top of a vertical reactor with cylindrical shape and made of pyrex:

a first height of 1 ml of silicon carbide in the form of particles of 0.125 mm in diameter, a second height of 1 ml of silicon carbide in the form of particles of 0.062 mm in diameter, a third height of 5 g of catalyst in the form of particles of 0.02 to 1 mm diluted with 10 ml of silicon carbide in the form of particles of 0.062 mm in diameter, a fourth height of 1 ml of silicon carbide in the form of particles of 0.062 mm in diameter, a fifth height of 3 ml of silicon carbide in the form of particles of 0.125 mm in diameter and a sixth height of silicon carbide in the form of particles of 1.19 mm in diameter so as to fill all of the reactor.

b) Operating Method

The reactor is then heated to 250° C. and the vaporiser to 200° C. The electric initiation of the water pump is actuated.

Once the reactor and the vaporiser have reached the temperatures given above, the water pump is actuated and the temperature of the reactor is raised to the desired test temperature, i.e. 400° C.

The hot spot of the reactor is then left to stabilize for 30 minutes.

Then, oxygen is introduced in 10 pulses of 23 seconds each in order to sufficiently oxidize the catalyst. The catalyst is considered to be totally oxidized when the temperature of the hot spot has stabilized, i.e. when there is no more exothermal activity due to the reaction (by monitoring the catalyst temperature measured using a thermocouple placed in the catalyst bed, the fluctuations in temperature can be seen as a function of the pulses).

The pressure at the inlet of the reactor was approximately 1.1 to 1.8 bars (absolute) and the pressure drop across the reactor is approximately 0.1 to 0.8 bars (relative).

Test A

The production of acrylic acid was measured using a redox balance.

A redox balance is composed of 40 redox cycles. A redox cycle represents:

10 cycles of:

30 seconds of propane+5 seconds of oxygen (oxygen being injected at the start of the propane pulse), with the proportions propane/$O_2$/He—Kr/$H_2O$ of 10/10/45/45, with a helium-krypton flow of 4.292 Nl/h (Nl=liter of gas at 0° C. and 760 mm Hg);

an intermediate pulse composed only of the flow of carrier gas He—Kr/$H_2O$ of 45 seconds;

an oxygen pulse with the proportions $O_2$/He—Kr/$H_2O$=20/45/45 for 60 seconds and another intermediate pulse composed only of the flow of carrier gas He—Kr/$H_2O$ of 45 seconds;

10 cycles of:

30 seconds of propane+10 seconds of oxygen, with the proportions propane/$O_2$/He—Kr/$H_2O$ of 10/10/45/45, with a flow of helium-krypton of 4.292 Nl/h;

an intermediate pulse composed only of the flow of carrier gas He—Kr/$H_2O$ of 45 seconds;

an oxygen pulse with the proportions $O_2$/He—Kr/$H_2O$=20/45/45 for 60 seconds and another intermediate pulse composed only of the flow of carrier gas He—Kr/$H_2O$ of 45 seconds;

10 cycles of:

30 seconds of propane+15 seconds of oxygen, with the proportions propane/$O_2$/He—Kr/$H_2O$ of 10/10/45/45, with a flow of helium-krypton of 4.292 Nl/h;

an intermediate pulse composed only of the flow of carrier gas He—Kr/$H_2O$ of 45 seconds;

an oxygen pulse with the proportions $O_2$/He—Kr/$H_2O$=20/45/45 for 60 seconds and another intermediate pulse composed only of the flow of carrier gas He—Kr/$H_2O$ of 45 seconds; and 10 cycles of:

30 seconds of propane+20 seconds of oxygen, with the proportions propane/$O_2$/He—Kr/$H_2O$ of 10/10/45/45, with a flow of helium-krypton of 4.292 Nl/h;

an intermediate pulse composed only of the flow of carrier gas He—Kr/$H_2O$ of 45 seconds;

an oxygen pulse with the proportions $O_2$/He—Kr/$H_2O$=20/45/45 for 60 seconds and another intermediate pulse composed only of the flow of carrier gas He—Kr/$H_2O$ of 45 seconds.

During the balancing, four samples are taken, each representing 10 cycles. 4 samples of gas are also carried out using gas bags, each sample representing approximately 10 cycles. (The gas samples are carried out over a period corresponding to a multiple of the duration of a cycle, in order to be able to know the theoretical quantity of propane injected).

Each small gas-washing bottle (with a 25 ml capacity and filled with 20 ml of water) is equipped with a gas bag, and when the bottle is connected to the outlet of the reactor (as soon as the liquid bubbles), the bag is open and the chronometer is started.

In order to verify the oxidation state of the catalyst, another series of ten 23-second pulses of oxygen is carried out. It shows that the oxidation state of the solid has been maintained during the balancing (no exothermal activity).

The liquid effluents are analyzed on a BP 6890 chromatograph, after having carried out a specific calibration.

The gases are analyzed during the balancing on a Chrompack micro-GC chromatograph.

An assay of the acidity is carried out on each bottle during the operation, in order to determine the exact number of moles of acid produced and to validate the chromatographic analyses.

Test B

The procedure was undertaken as in test A, except that the redox balance was composed of the following 40 redox cycles:

10 cycles of:
30 seconds of propane+5 seconds of oxygen, (the oxygen being injected at the start of the propane pulse) with the proportions propane/$O_2$/He—Kr/$H_2O$ of 20/15/45/45, with a flow of helium-krypton of 4.292 N1/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds;

10 cycles of:
30 seconds of propane+10 seconds of oxygen, with the proportions propane/$O_2$/He—Kr/$H_2O$ of 20/15/45/45, with a flow of helium-krypton of 4.292 N1/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds;

10 cycles of:
30 seconds of propane+15 seconds of oxygen, with the proportions propane/$O_2$/He—Kr/$H_2O$ of 20/15/45/45, with a flow of helium-krypton of 4.292 N1/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds; and 10 cycles of:
30 seconds of propane+20 seconds of oxygen, with the proportions propane/$O_2$/He—Kr/$H_2O$ of 20/15/45/45, with a flow of helium-krypton of 4.292 N1/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds;

Test C

The procedure was the same as in test A, except that the redox balance was composed of the following 40 redox cycles:

10 cycles of:
30 seconds of propane+5 seconds of oxygen, (the oxygen being injected at the start of the propane pulse) with the proportions propane/$O_2$/He—Kr/$H_2O$ of 20/20/45/45, with a flow of helium-krypton of 4.292 N1/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds;

10 cycles of:
30 seconds of propane+10 seconds of oxygen, with the proportions propane/$O_2$/He—Kr/$H_2O$ of 20/10/45/45, with a flow of helium-krypton of 4.292 N1/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds;

10 cycles of:
30 seconds of propane+15 seconds of oxygen, with the proportions propane/$O_2$/He—Kr/$H_2O$ of 20/6.7/45/45, with a flow of helium-krypton of 4.292 N1/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds; and 10 cycles of:
30 seconds of propane+20 seconds of oxygen, with the proportions propane/$O_2$/He—Kr/$H_2O$ of 20/5/45/45, with a flow of helium-krypton of 4.292 N1/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds.

Test D

The procedure was the same as in test A, except that the redox balance was composed of the following 40 redox cycles:

10 cycles of:
30 seconds of propane+5 seconds of oxygen, (the oxygen being injected at the start of the propane pulse) with the proportions propane/$O_2$/He—Kr/$H_2O$ of 30/30/45/45, with a flow of helium-krypton of 4.292 N1/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds;

10 cycles of:
30 seconds of propane+10 seconds of oxygen, with the proportions propane/$O_2$/He—Kr/$H_2O$ of 30/15/45/45, with a flow of helium-krypton of 4.292 Nl/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds;
10 cycles of:
30 seconds of propane+15 seconds of oxygen, with the proportions propane/$O_2$/He—Kr/$H_2O$ of 30/10/45/45, with a flow of helium-krypton of 4.292 Nl/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds; and
10 cycles of:
30 seconds of propane+20 seconds of oxygen, with the proportions propane/$O_2$/He—Kr/$H_2O$ of 30/7.5/45/45, with a flow of helium-krypton of 4.292 Nl/h;
an intermediate pulse composed only of the flow of carrier gas He—Kr/$H_2O$ of 60 seconds;
an oxygen pulse with the proportions $O_2$/He—Kr/$H_2O$=20/45/45 for 60 seconds and
another intermediate pulse composed only of the flow of carrier gas He—Kr/$H_2O$ of 60 seconds;

c) Results

The final results correspond to the microbalances carried out on the 4 gas-washing bottles and the 4 gas bags.

In tests A and B, the quantity of oxygen injected was increasing when changing from one series of 10 cycles to another, because the duration of the oxygen pulse was increasing.

In tests C and D, the quantity of oxygen remained constant when changing from one series of 10 cycles to another. In fact, although the duration of the oxygen pulse increased form one series of 10 cycles to another, the proportion of oxygen in the pulse was adjusted (reduced) each time.

The results are compiled in the following Tables I and II:

TABLE I

| | \multicolumn{16}{c}{TEST} | | | | | | | | | | | | | | | |
|---|---|---|---|---|---|---|---|---|---|---|---|---|---|---|---|---|
| | A | | | | B | | | | C | | | | D | | | |
| In the reaction: propane + oxygen/ He—Kr/$H_2O$ Selectivities (%) | 10 + 10/45/45 | | | | 20 + 15/45/45 | | | | 20 + (20/10/6.7/5)45/45 | | | | 30 + (30/15/10/7.5)/45/45 | | | |
| Duration of the oxygen pulses injected into the propane pulses | 5 | 10 | 15 | 20 | 5 | 10 | 15 | 20 | 5 | 10 | 15 | 20 | 5 | 10 | 15 | 20 |
| Acrylic acid | 45.2 | 48.6 | 50.1 | 56.2 | 39.9 | 41.6 | 45.8 | 49.0 | 35.0 | 35.9 | 31.7 | 28.2 | 33.9 | 35.1 | 29.1 | 28.6 |
| Acetic acid | 10.7 | 8.9 | 10.2 | 8.1 | 10.9 | 9.9 | 8.7 | 8.9 | 11.9 | 12.2 | 13.1 | 13.6 | 12.8 | 12.9 | 14.8 | 16.0 |
| Acrolein | 0.16 | 0.15 | 0.15 | 0.15 | 0.12 | 0.10 | 0.10 | 0.10 | 0.08 | 0.08 | 0.08 | 0.08 | 0.09 | 0.09 | 0.09 | 0.09 |
| Acetone | 0.58 | 0.53 | 0.52 | 0.51 | 0.81 | 0.67 | 0.58 | 0.54 | 0.78 | 0.74 | 0.81 | 0.78 | 0.96 | 1.00 | 1.14 | 1.24 |
| Propionic acid | 0.24 | 0.28 | 0.28 | 0.25 | 0.22 | 0.22 | 0.21 | 0.20 | 0.21 | 0.96 | 0.22 | 0.21 | 0.33 | 0.66 | 0.23 | 0.25 |
| Allyl alcohol | 0.04 | 0.06 | 0.08 | 0.06 | 0.03 | 0.03 | 0.03 | 0.04 | 0.02 | 0.02 | 0.02 | 0.02 | 0.01 | 0.02 | 0.02 | 0.02 |
| Allyl acrylate | 0.00 | 0.09 | 0.10 | 0.11 | 0.04 | 0.10 | 0.04 | 0.10 | 0.00 | 0.00 | 0.00 | 0.00 | 0.00 | 0.00 | 0.00 | 0.00 |
| Propyl aldehyde | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| Acetaldehyde | 0.05 | 0.00 | 0.00 | 0.00 | 0.04 | 0.04 | 0.03 | 0.03 | 0.03 | 0.03 | 0.03 | 0.03 | 0.03 | 0.03 | 0.04 | 0.04 |
| CO | 15.3 | 15.1 | 14.4 | 12.8 | 16.1 | 16.1 | 15.6 | 15.1 | 17.7 | 16.8 | 18.2 | 19.0 | 15.6 | 15.0 | 16.4 | 15.7 |
| $CO_2$ | 15.9 | 14.7 | 12.8 | 11.4 | 18.1 | 17.1 | 15.4 | 13.5 | 20.0 | 19.2 | 21.0 | 23.1 | 18.3 | 17.8 | 20.0 | 19.9 |
| Propylene | 11.8 | 11.6 | 11.4 | 10.4 | 13.7 | 14.2 | 13.5 | 12.4 | 14.2 | 14.1 | 14.8 | 15.1 | 18.0 | 17.3 | 18.3 | 18.1 |
| Selectivity in acrylic acid | 45.2 | 48.6 | 50.1 | 56.2 | 39.9 | 41.6 | 45.8 | 49.0 | 35.0 | 35.9 | 31.7 | 28.2 | 33.9 | 35.1 | 29.1 | 28.6 |
| Selectivity in acrylic acid and propylene | 57.0 | 60.2 | 61.5 | 66.6 | 53.5 | 55.8 | 59.2 | 61.4 | 49.2 | 50.0 | 46.6 | 43.3 | 51.9 | 52.5 | 47.3 | 46.7 |

TABLE II

| | \multicolumn{8}{c}{TEST} | | | | | | | |
|---|---|---|---|---|---|---|---|---|
| | A | | | | B | | | |
| In the reaction: propane + oxygen/ He—Kr/$H_2O$ Selectivities (%) | 10 + 10/45/45 | | | | 20 + 15/45/45 | | | |
| Duration of the oxygen pulses injected into the propane pulses Yields (%) | 5 | 10 | 15 | 20 | 5 | 10 | 15 | 20 |
| Acrylic acid | 11.75 | 13.05 | 14.04 | 16.73 | 9.14 | 9.54 | 11.16 | 12.99 |
| Acetic acid | 2.77 | 2.40 | 2.85 | 2.41 | 2.51 | 2.26 | 2.13 | 2.37 |

TABLE II-continued

| | | | | | | | | |
|---|---|---|---|---|---|---|---|---|
| Acrolein | 0.04 | 0.04 | 0.04 | 0.05 | 0.03 | 0.02 | 0.02 | 0.03 |
| Acetone | 0.15 | 0.14 | 0.15 | 0.15 | 0.19 | 0.15 | 0.14 | 0.14 |
| Propionic acid | 0.06 | 0.07 | 0.08 | 0.07 | 0.05 | 0.05 | 0.05 | 0.05 |
| Allyl alcohol | 0.01 | 0.02 | 0.02 | 0.02 | 0.01 | 0.01 | 0.01 | 0.01 |
| Allyl acrylate | 0.00 | 0.02 | 0.03 | 0.03 | 0.01 | 0.02 | 0.01 | 0.03 |
| Propyl aldehyde | 0.00 | 0.00 | 0.00 | 0.00 | 0.00 | 0.00 | 0.00 | 0.00 |
| Acetaldehyde | 0.01 | 0.00 | 0.00 | 0.00 | 0.01 | 0.01 | 0.01 | 0.01 |
| CO | 3.98 | 4.06 | 4.04 | 3.82 | 3.70 | 3.68 | 3.80 | 4.01 |
| $CO_2$ | 4.14 | 3.94 | 3.59 | 3.41 | 4.15 | 3.93 | 3.76 | 3.58 |
| Propylene | 3.06 | 3.12 | 3.19 | 3.09 | 3.13 | 3.25 | 3.28 | 3.28 |
| Propane | 73.55 | 72.65 | 71.76 | 69.72 | 77.20 | 77.14 | 75.55 | 73.59 |
| Carbon balance (%) | 99.53 | 99.52 | 99.79 | 99.49 | 100.12 | 100.09 | 99.92 | 100.09 |
| Quantity of oxygen consumed (g O/kg catalyst) | 1.64 | 1.73 | 1.79 | 1.88 | 2.77 | 2.85 | 2.97 | 3.18 |
| µmole propane for 1 cycle | 390 | 406 | 412 | 417 | 735 | 767 | 767 | 769 |
| µmole $O_2$ added per cycle | 53 | 107 | 160 | 214 | 107 | 214 | 320 | 427 |
| µmole O consumed (products formed)/cycle | 511 | 542 | 559 | 589 | 865 | 891 | 929 | 994 |
| Propane conversion ratio (kg catalyst/kg propane converted) | 1058 | 1023 | 991 | 924 | 650 | 649 | 606 | 561 |

| | TEST | | | | | | | |
|---|---|---|---|---|---|---|---|---|
| | C | | | | D | | | |
| In the reaction: propane + oxygen/He—Kr/$H_2O$ Selectivities (%) | 20 + (20/10/6.7/5)45/45 | | | | 30 + (30/15/10/7.5)/45/45 | | | |
| Duration of the oxygen pulses injected into the propane pulses Yields (%) | 5 | 10 | 15 | 20 | 5 | 10 | 15 | 20 |
| Acrylic acid | 7.84 | 8.15 | 6.95 | 6.07 | 6.55 | 7.06 | 5.59 | 5.52 |
| Acetic acid | 2.67 | 2.76 | 2.87 | 2.92 | 2.48 | 2.59 | 2.84 | 3.10 |
| Acrolein | 0.02 | 0.02 | 0.02 | 0.02 | 0.02 | 0.02 | 0.02 | 0.02 |
| Acetone | 0.17 | 0.17 | 0.18 | 0.17 | 0.19 | 0.20 | 0.22 | 0.24 |
| Propionic acid | 0.05 | 0.22 | 0.05 | 0.05 | 0.06 | 0.13 | 0.05 | 0.05 |
| Allyl alcohol | 0.00 | 0.00 | 0.00 | 0.01 | 0.00 | 0.00 | 0.00 | 0.00 |
| Allyl acrylate | 0.00 | 0.00 | 0.00 | 0.00 | 0.00 | 0.00 | 0.00 | 0.00 |
| Propyl aldehyde | 0.00 | 0.00 | 0.00 | 0.00 | 0.00 | 0.00 | 0.00 | 0.00 |
| Acetaldehyde | 0.01 | 0.01 | 0.01 | 0.01 | 0.01 | 0.01 | 0.01 | 0.01 |
| CO | 3.96 | 3.81 | 3.98 | 4.08 | 3.00 | 3.02 | 3.15 | 3.04 |
| $CO_2$ | 4.48 | 4.37 | 4.60 | 4.96 | 3.53 | 3.58 | 3.84 | 3.85 |
| Propylene | 3.18 | 3.20 | 3.25 | 3.26 | 3.47 | 3.49 | 3.51 | 3.50 |
| Propane | 77.69 | 77.38 | 78.21 | 78.44 | 80.63 | 79.89 | 80.88 | 80.73 |
| Carbon balance (%) | 100.09 | 100.10 | 100.10 | 99.98 | 99.93 | 99.99 | 100.11 | 100.06 |
| Quantity of oxygen consumed (g O/kg catalyst) | 2.77 | 2.84 | 2.85 | 2.89 | 3.59 | 3.79 | 3.71 | 3.70 |
| µmole propane for 1 cycle | 732 | 752 | 762 | 764 | 1162 | 1184 | 1178 | 1175 |
| µmole $O_2$ added per cycle | 107 | 107 | 107 | 107 | 161 | 161 | 161 | 161 |
| µmole O consumed (products formed)/cycle | 867 | 889 | 892 | 902 | 1122 | 1184 | 1158 | 1157 |
| Propane conversion ratio (kg catalyst/kg propane converted) | 678 | 669 | 694 | 701 | 495 | 477 | 502 | 498 |

From Table I above the following observations can be drawn:

- in the same test A or B, the larger the quantity of oxygen injected, the higher the acrylic acid selectivity;
- tests C and D show that it is better to have a high partial pressure of oxygen for a short time than the same quantity of oxygen for a longer time.

From Table II the following observations can be drawn:

- the quantity of oxygen consumed, calculated on the basis of the products formed, does not increase much with the addition of molecular oxygen and the conversion does not change much with the addition of molecular oxygen;

the quantity of oxygen consumed (in µmoles of atomic oxygen) is greater than the quantity added by the pulse; this means that the catalyst was reduced in any case;
the conversion is higher in Test A;
the lowest conversion ratio is obtained when the partial pressure of propane is highest.

Example 3

Comparative

A catalyst was prepared in the following way.

5.35 g of ammonium paramolybdate and 0.80 g of tellurium dioxide ($TeO_2$) are successively added under stirring into 20 ml of water. Separately, a solution containing 15 mmoles of vanadium is prepared by dissolving 3.94 g of hydrated vanadyl sulphate in 20 ml of distilled water. The two solutions are then slowly mixed and stirred for 10 minutes before being introduced into a 70 ml autoclave covered with Teflon®. Then nitrogen is bubbled through for 5 minutes so that it substitutes the air present in the autoclave, before the latter is closed. The autoclave is then set at 175° C. for 72 hours.

After this period, the autoclave is cooled with water under the tap for 10 minutes. The black solid obtained in the autoclave is separated from the solution by filtration, thoroughly washed with distilled water and dried for 12 hours at 80° C. The precursor thus obtained is then precalcinated under air at 280° C. for 2 hours. Then, the solid obtained is calcinated under nitrogen flow (25 ml/h/g) at 600° C. for 2 hours. In this way catalyst 3 is obtained.

Test Conditions 500 mg of catalyst 3 are vigorously ground and poured into a reactor made of Pyrex®. The selective oxidation reaction for propane is carried out at atmospheric pressure, in a reactor under a conventional flow. The gaseous reaction mixture propane/oxygen/nitrogen/water vapour (6.5%/10%/38%/45%) is introduced into the reactor maintaining a contact time of 2.1 s. The catalyst is tested at 320 and 360° C. The results are compiled in Tables 2 and 3.

Example 4

A catalyst was prepared in the following way.

4.32 g of molybdenum oxide, 0.80 g of tellurium dioxide ($TeO_2$) and 0.82 g of vanadium oxide $V_2O_5$ are added successively and under stirring to 30 ml of water heated to 80° C. Separately, a solution containing 3.6 mmoles of niobium is prepared by dissolving under stirring, 2.33 g of hydrated niobium oxalate in 10 ml of distilled water heated to 80° C. The two solutions are then slowly mixed and stirred for 10 minutes before being introduced into a 70 ml autoclave covered with Teflon®. Then nitrogen is bubbled through for 5 minutes so that it replaces the air present in the autoclave, before the latter is closed. The autoclave is then set at 175° C. for 48 hours.

After this time, the autoclave is cooled down with tap water, for 10 minutes. The black-blue solid obtained in the autoclave is separated from the solution by filtration, washed thoroughly with distilled water and dried for 12 hours at 80° C. The precursor thus obtained is then calcinated under nitrogen flow (25 ml/h/g) at 600° C. for 2 hours. In this way catalyst 4 is obtained. This catalyst is tested under the same conditions as catalyst 3. The results are compiled in Tables 2 and 3.

Example 5

A catalyst was prepared in the following way.

5.35 g of ammonium paramolybdate and 1.16 g of telluric acid are successively added to 20 ml of water heated to 80° C. under stirring. Separately, a solution containing 9 mmoles of vanadium is prepared by dissolving 2.37 g of hydrated vanadyl sulphate in 10 ml of distilled water heated to 80° C. A third solution containing 3.6 mmole of niobium is simultaneously prepared by dissolving under stirring, 2.33 g of hydrated niobium oxalate in 10 ml of distilled water heated to 80° C. The second solution is added to the first and the mixture is stirred for 5 minutes. Finally the third solution is added and the mixture is then stirred for 10 minutes before being introduced into a 70 ml autoclave covered with Teflon®. Then nitrogen is bubbled through for 5 minutes so that it substitutes the air present in the autoclave, before the latter is closed. The autoclave is then set at 175° C. for 48 hours.

After this time, the autoclave is cooled down with tap water, for 10 minutes. The black-blue solid obtained in the autoclave is separated from the solution by filtration, washed thoroughly with distilled water and dried for 12 hours at 80° C. The precursor thus obtained is then calcinated under nitrogen flow (25 ml/h/g) at 600° C. for 2 hours. In this way catalyst 5 is obtained. This catalyst is tested under the same conditions as catalyst 3. The results are compiled in Tables 2 and 3.

Example 6

A catalyst was prepared in the following way.

5.35 g of ammonium paramolybdate is added to 20 ml of water heated to 80° C. under stirring. Separately, a solution containing 15 mmoles of vanadium is prepared by dissolving 3.94 g of hydrated vanadyl sulphate in 20 ml of distilled water heated to 80° C. The second solution is added to the first and the mixture is then stirred for 10 minutes before being introduced into a 70 ml autoclave covered with Teflon®. Then nitrogen is bubbled through for 5 minutes so that it substitutes the air present in the autoclave, before the latter is closed. The autoclave is then set at 175° C. for 24 hours.

After this time, the autoclave is cooled down with tap water, for 10 minutes. The black-blue solid obtained in the autoclave is separated from the solution by filtration, washed thoroughly with distilled water and dried for 12 hours at 80° C. The precursor thus obtained is then calcinated under nitrogen flow (25 ml/h/g) at 500° C. for 2 hours. In this way catalyst 6 is obtained. This catalyst is tested under the same conditions as catalyst 3.

According to a similar operating method, tellurium can be introduced into this preparation.

TABLE 1

Summary table of the different preparations

| Example No. | Composition of the solution (without oxygen) | Method of preparation |
| --- | --- | --- |
| Example 3 | $Mo_{1.0}V_{0.50}Te_{0.16}$ | Hydrothermal synthesis |
| Example 4 | $Mo_{1.0}V_{0.50}Te_{0.16}Nb_{0.12}$ | Hydrothermal synthesis |
| Example 5 | $Mo_{1.0}V_{0.30}Te_{0.16}Nb_{0.12}$ | Hydrothermal synthesis |
| Example 6 | $Mo_{1.0}V_{0.50}$ | Hydrothermal synthesis |

TABLE 2

Oxidation of propane at 320° C. on tellurium catalysts

| Example No. | Conversion (%) C$_3$H$_8$ | Selectivity (%) | | | | | | Yield (%) Acrylic acid |
|---|---|---|---|---|---|---|---|---|
| | | Acrylic acid | C$_3$H$_6$ | Acetone | Acetic acid | CO | CO$_2$ | |
| 3 | 17.1 | 50.1 | 13.5 | 6.00 | 13.6 | 9.25 | 7.55 | 7.72 |
| 4 | 15.7 | 62.8 | 19.4 | 2.47 | 6.65 | 5.20 | 3.47 | 9.86 |
| 5 | 16.2 | 59.5 | 16.1 | 2.77 | 9.57 | 7.20 | 4.88 | 9.62 |
| 6 | 11.1 | 5.41 | 19.5 | 0.97 | 20.4 | 33.1 | 20.6 | 0.60 |

TABLE 3

Oxidation of propane at 360° C. on tellurium catalysts

| Example No. | Conversion (%) C$_3$H$_8$ | Selectivity (%) | | | | | | Yield (%) Acrylic acid |
|---|---|---|---|---|---|---|---|---|
| | | Acrylic acid | C$_3$H$_6$ | Acetone | Acetic acid | CO | CO$_2$ | |
| 3 | 36.2 | 47.3 | 7.49 | 1.33 | 16.7 | 14.0 | 13.3 | 16.3 |
| 4 | 25.5 | 69.0 | 8.83 | 0.40 | 5.03 | 9.22 | 7.52 | 24.5 |
| 5 | 33.4 | 62.4 | 8.72 | 0.45 | 7.27 | 11.1 | 10.1 | 20.8 |
| 6 | 23.4 | 4.21 | 11.4 | 0.27 | 14.8 | 41.4 | 27.9 | 0.98 |

In the case of Examples 3 and 5, the effluents of the test are collected for 4 hours in an ice-trap. 2 analyses by chromatography coupled with a mass spectrometer are carried out per sample.

5 main products are detected per sample: acetone, water, acetic acid, propionic acid and acrylic acid.

The molar ratios propionic acid/acrylic acid are thus calculated for each sample, for reaction temperatures of 320° C. and 360° C. The average of the two analyses carried out per sample is given in Table 4 below.

TABLE 4

Molar ratio Propionic acid/Acrylic acid

| Example | 320° C. | 360° C. |
|---|---|---|
| 3 | 6.74% | 2.12% |
| 5 | 6.43% | 0.92% |

It is noted that the molar ratio decreases with an increase in the temperature. But also this ratio is still smaller for the catalysts containing niobium.

Similarly as regards the acetone selectivity, this is even smaller when the catalyst contains niobium.

Example 7

In one example the catalyst prepared in Example 1 was tested again. This catalyst has a particle size of less than 40 μm.

Then a reactor was loaded as shown in Example 2a) and operated according to the operating method shown in Example 2b).

i) Test E

In this test the oxidation of t propane is carried out at 400° C.

The duration of oxygen injection into the propane pulse is varied maintaining constant propane and oxygen pressure.

The oxygen is injected at the end of the propane pulse to see if there is an influence on the catalytic performances compared to an injection at the start of the pulse.

The balance of 40 cycles is broken down as follows:

10 cycles of 30 s of propane+20 s of O$_2$ (the oxygen being injected at the end of the propane pulse), with the proportions propane/O$_2$/He—Kr/H$_2$O of 30/30/45/45, with a flow of helium-krypton of 4.27 Nl/h.

There is then an intermediate pulse composed only of the flow of carrier gas He—Kr/H$_2$O of 60 s, then a pulse of O$_2$ with the proportions O$_2$/He—Kr/H$_2$O=20/45/45 for 60 s and another pulse of carrier gas of 60 s.

Then there is another series of 10 cycles of 30 s of propane+15 s of oxygen with the proportions propane/O$_2$/He—Kr/H$_2$O of 30/30/45/45, with a helium-krypton flow of 4.27 Nl/h. Then there is an intermediate pulse composed only of the carrier gas He—Kr/H$_2$O of 60 s, then an oxygen pulse with the proportions O$_2$/He—Kr/H$_2$O=20/45/45, for 60 s and another intermediate pulse of carrier gas of 60 s.

Then there is another series of 10 cycles of 30 s of propane+10 s of O$_2$ with the proportions propane/O$_2$/He—Kr/H$_2$O of 30/30/45/45, with a helium-krypton flow of 4.27 Nl/h. Then there is an intermediate pulse composed only of the flow of carrier gas He—Kr/H$_2$O of 60 s, then a pulse of O$_2$ with the proportions O$_2$/He—Kr/H$_2$O=20/45/45, for 60 s and another intermediate pulse of carrier gas of 60 s.

Then there is another series of 10 cycles of 30 s of propane+5 s of O$_2$ with the proportions propane/O$_2$/He—Kr/H$_2$O of 30/30/45/45, with a helium-krypton flow of 4.27 Nl/h. Then there is an intermediate pulse composed only of the flow of carrier gas He—Kr/H$_2$O of 60 s, then a pulse of O$_2$ with the proportions O$_2$/He—Kr/H$_2$O=20/45/45, for 60 s and another intermediate pulse of carrier gas of 60 s.

ii) Test F

In this test, the oxidation of the propane is also carried out at 400° C.

The effect of the oxygen injection is compared at the end and at the start of the propane pulse maintaining constant propane and oxygen pressures but also a constant duration of oxygen injection in the propane pulse.

The balance of 40 cycles is broken down as follows:

10 cycles of 30 s of propane+20 s of O$_2$ (the oxygen being injected at the end of the propane pulse), with the proportions propane/O$_2$/He—Kr/H$_2$O of 30/30/45/45, with a helium-krypton flow of 4.27 Nl/h. Then there is an intermediate pulse composed only of the flow of carrier gas He/Kr/H$_2$O of 60 s, then an intermediate pulse of O$_2$ with the proportions O$_2$/He—Kr/H$_2$O=20/45/45 for 60 s and another intermediate pulse of carrier gas of 60 s.

Then there is another series of 10 cycles of 30 s of propane+20 s of oxygen (O$_2$ being injected at the end of the propane pulse) with the proportions propane/O$_2$/He—Kr/H$_2$O of 30/30/45/45, with a helium-krypton flow of 4.27 Nl/h. Then there is an intermediate pulse composed only of the flow of carrier gas He—Kr/H$_2$O of 60 s, then an intermediate pulse of oxygen with the proportions $O_2$/He—Kr/$H_2O$=20/45/45, for 60 s and another intermediate pulse of carrier gas of 60 s.

10 cycles of 30 s of propane+20 s of $O_2$ (the oxygen being injected at the start of the propane pulse), with the proportions propane/$O_2$/He—Kr/$H_2O$ of 30/30/45/45, with a helium-krypton flow of 4.27 Nl/h. Then there is an intermediate pulse composed only of the flow of carrier gas He—Kr/$H_2O$ of 60 s, then an intermediate pulse of $O_2$ with the proportions $O_2$/He—Kr/$H_2O$=20/45/45, for 60 s and another intermediate pulse of carrier gas of 60 s.

Then there is another series of 10 cycles of 30 s of propane+20 s of $O_2$ (the oxygen being injected at the start of the propane pulse), with the proportions propane/$O_2$/He—Kr/$H_2O$ of 30/30/45/45, with a helium-krypton flow of 4.27 Nl/h. Then there is an intermediate pulse composed only of the flow of carrier gas He—Kr/$H_2O$ of 60 s, then an intermediate pulse of $O_2$ with the proportions $O_2$/He—Kr/$H_2O$=20/45/45, for 60 s and another intermediate pulse of carrier gas of 60 s.

iii) Test G

This test was carried out in a similar way to test F.

iv) Results of the tests

TABLE 5

| | Test | | | | | | | | | | | |
|---|---|---|---|---|---|---|---|---|---|---|---|---|
| | E | | | | G | | | | F | | | |
| Conditions in the reaction: propane/He—Kr/$H_2O$ | 30 + 30/45/45 | | | | 30 + 30/45/45 | | | | 30 + 30/45/45 | | | |
| Conditions in regeneration $O_2$/He—Kr/$H_2O$ | 20/45/45 | | | | 20/45/45 | | | | 20/45/45 | | | |
| Comments | Variation in the duration of the injection of oxygen in the propane pulse. Injection of oxygen at the end of the pulse | | | | Duration of $O_2$ injection into the constant propane pulse injection of $O_2$ at the end of the pulse then at the start of the pulse | | | | Duration of $O_2$ injection into the constant propane pulse injection of $O_2$ at the end of the pulse then at the start of the pulse | | | |
| Recapitulative | Flask 1 | Flask 2 | Flask 3 | Flask 4 | Flask 1 | Flask 2 | Flask 3 | Flask 4 | Flask 1 | Flask 2 | Flask 3 | Flask 4 |
| Number of CYCLES | 10 | 10 | 10 | 10 | 10 | 10 | 10 | 10 | 10 | 10 | 10 | 10 |
| Duration of the propane injection | 33.2 | 33.9 | 32.8 | 33.5 | 33.9 | 34.2 | 34.7 | 33.8 | 34.3 | 35.1 | 35.2 | 34.9 |
| Duration of the oxygen pulses injected into the propane | 20 | 15 | 10 | 5 | 20 | 20 | 20 | 20 | 20 | 20 | 20 | 20 |
| Yields (%) | | | | | | | | | | | | |
| Acetaldehyde | 0.01 | 0.01 | 0.01 | 0.01 | 0.01 | 0.01 | 0.00 | 0.00 | 0.01 | 0.01 | 0.00 | 0.00 |
| Propyl aldehyde | 0.00 | 0.00 | 0.00 | 0.00 | 0.00 | 0.00 | 0.00 | 0.00 | 0.00 | 0.00 | 0.00 | 0.00 |
| Acetone | 0.06 | 0.07 | 0.09 | 0.10 | 0.06 | 0.07 | 0.06 | 0.06 | 0.06 | 0.07 | 0.06 | 0.06 |
| Acrolein | 0.02 | 0.02 | 0.02 | 0.01 | 0.02 | 0.02 | 0.02 | 0.02 | 0.02 | 0.02 | 0.02 | 0.02 |
| Allyl alcohol | 0.00 | 0.00 | 0.00 | 0.00 | 0.00 | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 | 0.00 | 0.00 | 0.00 | 0.00 | 0.00 |
| Acetic acid | 1.62 | 1.93 | 2.47 | 2.75 | 2.02 | 2.07 | 2.12 | 2.13 | 2.40 | 2.55 | 2.36 | 2.49 |
| Propionic acid | 0.05 | 0.05 | 0.06 | 0.06 | 0.04 | 0.05 | 0.05 | 0.05 | 0.05 | 0.05 | 0.05 | 0.05 |
| Acrylic acid | 12.56 | 10.73 | 7.80 | 6.17 | 12.40 | 12.31 | 12.11 | 12.47 | 11.28 | 11.60 | 11.30 | 11.74 |
| Carbon monoxide | 2.78 | 2.64 | 2.74 | 2.63 | 3.79 | 3.14 | 3.56 | 3.71 | 4.11 | 3.94 | 4.28 | 4.28 |
| Carbon dioxide | 2.37 | 2.74 | 3.43 | 3.71 | 3.64 | 2.95 | 3.84 | 3.98 | 3.81 | 3.74 | 4.37 | 4.43 |
| Propylene | 3.63 | 3.43 | 3.42 | 3.50 | 3.40 | 3.48 | 3.57 | 3.52 | 3.36 | 3.41 | 3.52 | 3.49 |
| Propane | 77.25 | 78.57 | 79.75 | 81.16 | 74.80 | 76.16 | 74.96 | 74.41 | 74.97 | 74.82 | 74.13 | 73.71 |
| Carbon balance (%) | 100.3 | 100.2 | 99.8 | 100.1 | 100.2 | 100.3 | 100.3 | 100.3 | 100.1 | 100.2 | 100.1 | 100.3 |

TABLE 6

| | Test | | | | | | | | | | | |
|---|---|---|---|---|---|---|---|---|---|---|---|---|
| | E | | | | G | | | | F | | | |
| Conditions in the reaction: propane + oxygen/ He—Kr/$H_2O$ | 30 + 30/45/45 | | | | 30 + 30/45/45 | | | | 30 + 30/45/45 | | | |
| Conditions in regeneration $O_2$/He—Kr/$H_2O$ | 20/45/45 | | | | 20/45/45 | | | | 20/45/45 | | | |
| Comments | Variation in the duration of the injection of $O_2$ in the propane pulse. Injection of $O_2$ at the end of the pulse | | | | Duration of $O_2$ injection into the constant propane pulse injection of $O_2$ at the end of the pulse then at the start of the pulse | | | | Duration of $O_2$ injection into the constant propane pulse injection of $O_2$ at the end of the pulse then at the start of the pulse | | | |
| Recapitulative | Flask 1 | Flask 2 | Flask 3 | Flask 4 | Flask 1 | Flask 2 | Flask 3 | Flask 4 | Flask 1 | Flask 2 | Flask 3 | Flask 4 |
| Number of cycles | 10 | 10 | 10 | 10 | 10 | 10 | 10 | 10 | 10 | 10 | 10 | 10 |

TABLE 6-continued

| | Test | | | | | | | | | | | |
|---|---|---|---|---|---|---|---|---|---|---|---|---|
| | E | | | | G | | | | F | | | |
| Duration of the propane injection | 33.2 | 33.9 | 32.8 | 33.5 | 33.9 | 34.2 | 34.7 | 33.8 | 34.3 | 35.1 | 35.2 | 34.9 |
| Duration of the oxygen pulses injected into the propane | 20 | 15 | 10 | 5 | 20 | 20 | 20 | 20 | 20 | 20 | 20 | 20 |
| Selectivities (%) | | | | | | | | | | | | |
| Acetaldehyde | 0.04 | 0.03 | 0.04 | 0.03 | 0.03 | 0.02 | 0.02 | 0.02 | 0.02 | 0.02 | 0.02 | 0.02 |
| Propyl aldehyde | 0.00 | 0.00 | 0.00 | 0.00 | 0.00 | 0.00 | 0.00 | 0.00 | 0.00 | 0.00 | 0.00 | 0.00 |
| Acetone | 0.25 | 0.32 | 0.45 | 0.52 | 0.25 | 0.29 | 0.24 | 0.23 | 0.26 | 0.28 | 0.21 | 0.22 |
| Acrolein | 0.09 | 0.09 | 0.08 | 0.08 | 0.08 | 0.08 | 0.07 | 0.07 | 0.07 | 0.07 | 0.06 | 0.07 |
| Allyl alcohol | 0.00 | 0.00 | 0.00 | 0.00 | 0.00 | 0.00 | 0.01 | 0.00 | 0.00 | 0.00 | 0.01 | 0.01 |
| Allyl acrylate | 0.00 | 0.00 | 0.00 | 0.00 | 0.00 | 0.00 | 0.00 | 0.00 | 0.00 | 0.00 | 0.00 | 0.00 |
| Acetic acid | 7.01 | 8.93 | 12.31 | 14.53 | 7.95 | 8.59 | 8.36 | 8.22 | 9.54 | 10.05 | 9.10 | 9.39 |
| Propionic acid | 0.22 | 0.24 | 0.28 | 0.32 | 0.17 | 0.22 | 0.19 | 0.19 | 0.19 | 0.21 | 0.18 | 0.19 |
| Acrylic acid | 54.35 | 49.62 | 38.93 | 32.57 | 48.85 | 51.08 | 47.81 | 48.07 | 44.95 | 45.69 | 43.53 | 44.18 |
| Carbon monoxide | 12.04 | 12.23 | 13.69 | 13.88 | 14.92 | 13.04 | 14.07 | 14.29 | 16.39 | 15.51 | 16.49 | 16.11 |
| Carbon dioxide | 10.28 | 12.68 | 17.13 | 19.58 | 14.34 | 12.22 | 15.15 | 15.35 | 15.19 | 14.73 | 16.83 | 16.68 |
| Propylene | 15.71 | 15.86 | 17.09 | 18.50 | 13.39 | 14.46 | 14.08 | 13.57 | 13.39 | 13.43 | 13.56 | 13.14 |
| Quantity of oxygen consumed (g O/kg catalyst) | 3.58 | 3.53 | 3.35 | 3.31 | 4.37 | 4.00 | 4.47 | 4.49 | 4.46 | 4.57 | 4.83 | 4.89 |
| μmole propane for 1 cycle | 1078 | 1101 | 1065 | 1088 | 1101 | 1111 | 1127 | 1098 | 1114 | 1140 | 1143 | 1133 |
| μmole $O_2$ added per cycle | 634 | 475 | 317 | 158 | 634 | 634 | 634 | 634 | 634 | 634 | 634 | 634 |
| μmole O consumed (products formed)/cycle | 1120 | 1105 | 1049 | 1034 | 1368 | 1253 | 1399 | 1405 | 1396 | 1429 | 1511 | 1531 |
| Propane conversion ratio (kg catalyst/kg propane converted) | 454 | 482 | 510 | 549 | 407 | 430 | 409 | 400 | 399 | 396 | 386 | 380 |

It is seen that the catalytic performances of the catalyst are slightly better when the oxygen is injected at the end of the propane pulse. The oxygen injected at this time allows reoxidizing of the already reduced catalyst.

By adding the oxygen to the propane pulse, conversion ratios of the order of 380 to 400 kg/kg can be achieved with selectivities of acrylic acid of 45% and of propylene of 13% while having conversions of 26%.

Example 8

Preparation of the Precursors of Catalyst and Catalysts

I) Synthesis of the Precursor P1

This synthesis allows preparation of approximately 100 g of dry precursor.

a) Preparation of the Niobium Solution

In a 500 ml beaker, the following are introduced:
  88.0 g of demineralised water;
  15.9 g of oxalic acid i.e. noxalate=0.126 moles
  7.0 g of niobic acid i.e. nNb=0.042 moles giving an oxalate/niobium ratio=3

The solution is stirred while heating to 60° C. for 2 hours. However care is taken to not exceed a heating temperature of 80° C. in order to prevent the niobium oxalate formed from decomposing. At the start the solution is milky. During heating and stirring, the solution becomes less and less cloudy. It is left to cool to approximately 30° C. in ambient air while stirring continuously. In order to improve the limpidity, the solution is centrifuged at 6200 r.p.m. for 12 minutes. A white deposit of niobic acid is then observed.

b) Preparation of the Mo—V—Te Solution

In a 500 ml beaker, the following are introduced:
  292.2 g of demineralised water;
  19.1 g of telluric acid i.e. $n_{Te}$=0.083 moles
  14.6 g of MVA i.e. $n_v$=0.125 moles
  67.1 g of HMA i.e. $n_{Mo}$=0.380 moles At first the solution is an orange/yellow colour and cloudy. The mixture is stirred and heated to approximately 60° C. until a limpid red colouring is observed (i.e. approximately 30 minutes). Then it is left to cool down to 30° C. at ambient temperature while maintaining stirring.

c) Preparation of the Mo—V—Te—Nb—Si Gel 54.0 g of silica solution (i.e. $n_{Si}$=0.360 moles) is added to the limpid red solution of Mo—V—Te obtained previously. The solution becomes red/orange and thickens slightly. It is maintained under stirring. Then the centrifuged solution of niobium is introduced. A very rapid development of the mixture is observed. In fact, in a few minutes the solution becomes thicker and more orange. A gel forms. Attention must be paid to the vortex during thickening of the mixture. This can diminish and make the mixture even thicker. The stirring must then be increased. Stir again for 45 minutes.

d) Drying of the Solution

The orange gel is poured into a teflon-coated plate then placed in an oven at 130° C. overnight. A coarse brown/ black powder is then obtained which does not stick to the plate. The weight of precursor obtained is 122.6 g. Depending on the quantities introduced initially, the formula of the precursor is $MoV_{0.33}Te_{0.22}Nb_{0.11}Si_{0.95}(Oxalate)_{0.33}(NH_4)_{1.19}O_x$.

Other precursors P2, P3 and P4

Table 7 gives the quantities of reagents introduced for the preparation of 3 other precursors P2, P3 and P4. The same operations as previously were carried out and the same changes in colouring and appearance were observed for all these experiments.

TABLE 7

|  |  |  | Experiments | | |
|---|---|---|---|---|---|
|  |  |  | P2 | P3 | P4 |
| Solution of niobium | oxalic acid | mass (g) | 15.9 | 15.9 | 15.9 |
|  |  | $n_{oxalate}$ (mol) | 0.126 | 0.126 | 0.126 |
|  | niobic acid | mass (g) | 7.0 | 7.0 | 7.0 |
|  |  | $n_{Nb}$ (mol) | 0.042 | 0.042 | 0.042 |
|  | demineralised water | mass (g) | 88.1 | 88.3 | 88.3 |
| Solution of MoV—Te | HMA | mass (g) | 67.2 | 67.1 | 67.1 |
|  |  | $n_{Mo}$ (mol) | 0.381 | 0.380 | 0.380 |
|  | MVA | mass (g) | 14.7 | 14.6 | 14.7 |
|  |  | $n_v$ (mol) | 0.126 | 0.125 | 0.126 |
|  | telluric acid | mass (g) | 19.1 | 19.1 | 19.2 |
|  |  | $n_{Te}$ (mol) | 0.083 | 0.083 | 0.084 |
|  | demineralised water | mass (g) | 291.2 | 292.3 | 291.6 |
| Ludox | silice | mass (g) | 54.7 | 54.1 | 54.1 |
|  |  | $n_{Si}$ (mol) | 0.364 | 0.360 | 0.360 |

Precursors P2, P3 and P4 all have practically the same formula:

P2: $MoV_{0.33}Te_{0.22}Nb_{0.11}Si_{0.96}(Oxalate)_{0.33}(NH_4)_{1.19}O_x$

P3: $MoV_{0.33}Te_{0.22}Nb_{0.11}Si_{0.95}(Oxalate)_{0.33}(NH_4)_{1.19}O_x$

P4: $MoV_{0.33}Te_{0.22}Nb_{0.11}Si_{0.95}(Oxalate)_{0.33}(NH_4)_{1.19}O_x$

Loss by Combustion

This experiment aims to determine the quantity of niobic acid which did not dissolve during preparation of the niobium oxalate solution. During preparation of the precursor P4, the white deposit formed during the centrifugation was sampled. This deposit has a weight of 0.5 g. It is placed in a ceramic crucible. After evaporation in ambient air, the deposit weighs 0.4 g. The deposit is then subjected to a rise in temperature of 3° C./min, from 20 to 600° C. and left at 600° C. for one hour.

After this heating, there remains only an $Nb_2O_5$ solid which weighs 0.2 g. Thus there was a total loss of weight of 0.3 g.

Initially, 7.0 g of niobic acid at 79% or 7*0.79=5.53 g of $Nb_2O_5$ was introduced. Thus there was approximately 3.62% (=0.2/(7*0.79)*100) of niobic acid which was not dissolved. Most of the niobic acid is therefore dissolved.

II) Precalcination Under Air

A precalcination under air is then carried out. The aim of this stage, among other things, is to eliminate the ammonia produced by the ammonium heptamolybdate and the ammonium metavanadate. For this, 30 g of precursor is placed inside small steel cups and between two silica wool wads. Two parameters were adjusted during the operations:

the precalcination temperature: desired values 280; 300; 320 and 340° C.; and the flow rates of air being introduced: desired values 0; 10; 30; 50 ml/min/g of catalyst.

Only the precalcination time remains the same for all the experiments. It is fixed at 4 hours.

III) Calcination Under Nitrogen

A calcination under nitrogen is then carried out. The flow rate, the temperature and the calcination times are the same for all the operations.

The conditions are as follows:

a flow rate of nitrogen of 50 ml/min/g of catalyst.

a calcination temperature of 600° C.

a calcination time of 2 hours.

Table 8 gives a summary of the precalcination and calcinations conditions carried out on the different precursors.

TABLE 8

| Precursor | Temperature of precalcination (in ° C.) | Flow rate of air (in ml/min/g of catalyst) | Temperature of calcination (in ° C.) | Flow rate of nitrogen (in ml/min/g of catalyst) | Reference of the calcinate |
|---|---|---|---|---|---|
| P2 | 317 | 0 | 597 | 52.8 | B1 |
|  | 316 | 11.1 | 596 | 48.8 | B2 |
|  | 320 | 29.8 | 602 | 49.4 | B3 |
|  | 318 | 50.6 | 602 | 52.5 | B4 |
| P1 | 301 | 0 | 598 | 50.3 | A1 |
|  | 300 | 11.0 | 597 | 49.0 | A2 |
|  | 303 | 31.2 | 600 | 49.5 | A3 |
|  | 301 | 50.4 | 602 | 50.2 | A4 |
| P3 | 350 | 0 | 601 | 50.2 | C1 |
|  | 347 | 9.9 | 598 | 51.1 | C2 |
|  | 349 | 30.7 | 601 | 50.4 | C3 |
|  | 348 | 51.3 | 602 | 49.6 | C4 |
| P4 | 273 | 0 | 600 | 49.5 | D1 |
|  | 272 | 10.9 | 598 | 49.6 | D2 |
|  | 273 | 31.9 | 600 | 49.9 | D3 |
|  | 273 | 47.6 | 601 | 49.3 | D4 |

Example 9 a) Apparatus

In order to simulate the method according to the invention, simulations were carried out in the laboratory in a laboratory fixed bed reactor.

The following are loaded from the bottom to the top of a vertical reactor with cylindrical shape and made of pyrex:
- a first height of 2 ml of silicon carbide in the form of particles of 0.125 mm in diameter,
- a second height of 5.00 g of catalyst in the form of particles of 0.02 to 1 mm diluted with 10 ml of silicon carbide in the form of particles of 0.125 mm in diameter,
- a third height of 2 ml of silicon carbide in the form of particles of 0.125 mm in diameter, and
- a fourth height of silicon carbide in the form of particles of 1.19 mm in diameter, so as to fill all of the reactor.

b) Catalyst Tests

1) Operating Method

The reactor is heated to 250° C. and the vaporiser to 200° C. The electric initiation of the water pump is actuated. The flow rate of He—Kr is set at its nominal value of 4.25 Nl/h.

Once the reactor and the vaporiser have reached the temperatures shown above, the water pump is actuated. When the water is present at the outlet of the reactor, the flowmeters of propane and oxygen are actuated. The reactor temperature is raised to the desired temperature and left for 30 minutes so that the hot spot is stabilized.

A thermocouple is placed in the catalyst bed, the temperature of the hot spot can be read.

Then the measurements relating to the production of acrylic acid itself can be undertaken.

During each balance, liquid samples are taken. Gas samples are also taken in line.

Each gas-washing bottle with a capacity of 125 ml is filled with water and when the flask is connected at the outlet of the reactor (when the liquid bubbles), the chronometer is started.

The liquid effluents are analyzed on an HP 6890 chromatograph, after having carried out a specific calibration.

The gases are analyzed in line during the balancing on a Chrompack micro-GC chromatograph.

An assay of the acidity is carried out on each flask to determine the exact number of moles of acid produced during each balance and to validate the chromatographic analyses.

2) Test of the Catalysts Prepared in Example 8

Catalysts A1 to A4, B1 to B4, C1 to C4 and D1 to D4 were tested at 3 different temperatures: 380, 390 and 400° C.

The proportions of the constituents of the initial gaseous mixture were as follows (in molar ratios):

propane/oxygen/inert(He—Kr)/$H_2O$(vapour)=1/1/4.5/4.5 for a flow rate of He—Kr of 4.25 Nl/h The temperature giving the best results is 400° C.

The selectivities and yields obtained at this temperature are compiled in Tables 9 and 10 below. In these tables, the temperatures and the flow rates used in the precalcination of Example 8 as well as the temperatures of the oven and of the hot spot during the catalyst test are also given.

The yields and selectivities obtained for allyl alcohol and ally acrylate are nil. Consequently they do not appear in Tables 9 and 10.

Table 9 shows the yields of carbon ($TTU_c$), with $TTG_c=\Sigma TTU_c$ and $TTG_{O2}=\Sigma TTU_O$, the acidities measured per assay with soda, the carbon and oxygen balances.

Table 10 shows the carbon selectivities.

TABLE 9

| Catalyst | | D1 | D2 | D3 | D4 | A1 | A2 | A3 | A4 |
|---|---|---|---|---|---|---|---|---|---|
| Temperature of precalcination (° C.) | | 273 | 272 | 273 | 273 | 301 | 300 | 303 | 301 |
| Air flow rate (ml/min/g of catalyst) | | 0 | 1091 | 31.9 | 47.57 | 0 | 11 | 31.2 | 50.4 |
| Oven temperature (° C.) | | 400 | 400 | 400 | 400 | 400 | 400 | 400 | 400 |
| Hot spot temperature (° C.) | | 413.2 | 415.2 | 412.5 | 412.6 | 409 | 414.4 | 408.3 | 407.8 |
| Yields in carbons ($TTU_c$ - %) | Acetaldehyde | 0.01 | 0.01 | 0.01 | 0.01 | 0.01 | 0.01 | 0.01 | 0 |
| | Propanol | 0 | 0 | 0 | 0 | 0 | 0 | 0 | 0 |
| | Acetone | 0.07 | 0.05 | 0.06 | 0.06 | 0.09 | 0.07 | 0.03 | 0.01 |
| | Acrolein | 0.01 | 0.01 | 0.02 | 0.02 | 0.01 | 0.01 | 0.02 | 0.02 |
| | Acetic acid | 0.77 | 0.79 | 0.76 | 0.78 | 0.87 | 1.01 | 0.25 | 0.1 |
| | Propionic acid | 0.04 | 0.03 | 0.03 | 0.03 | 0.05 | 0.04 | 0.01 | 0.01 |
| | Acrylic acid | 6.15 | 15.66 | 14 | 13.71 | 8.35 | 13.17 | 3.3 | 1.18 |
| | CO | 1.1 | 3.17 | 2.23 | 2.11 | 1.24 | 2.03 | 0.5 | 0.2 |
| | $CO_2$ | 0.86 | 2.81 | 2.01 | 1.88 | 0.85 | 1.64 | 0.4 | 0.19 |
| | Propene | 3.92 | 3.65 | 3.53 | 3.57 | 4.3 | 3.96 | 2.28 | 1.61 |
| | Propane | 85.39 | 73.57 | 78.47 | 79.3 | 85.96 | 79.39 | 92.4 | 95.53 |
| | Oxygen | 73.69 | 38.21 | 49.72 | 53.12 | 71.76 | 54.66 | 88.13 | 95.6 |
| Carbon balance | | 98.3 | 99.7 | 101.1 | 101.5 | 101.7 | 101.3 | 99.2 | 98.8 |
| Total carbon yield (TTG carbon) | | 12.9 | 26.2 | 22.6 | 22.2 | 15.8 | 22 | 6.8 | 3.3 |
| Oxygen balance | | 97.8 | 98.2 | 99 | 100.8 | 101.1 | 100.5 | 100.2 | 100.6 |
| Total oxygen yield ($TTG_m$) | | 24.1 | 60 | 49.3 | 47.7 | 29.4 | 45.8 | 12.1 | 5 |
| Acidity measured (assay AB)* (ppm) | | 3051.9 | 6160.6 | 5210.4 | 5481.8 | 3546.4 | 5651.8 | 408.3 | 513.9 |

| Catalyst | | B1 | B2 | B3 | B4 | C1 | C2 | C3 | C4 |
|---|---|---|---|---|---|---|---|---|---|
| Temperature of precalcination (° C.) | | 317 | 316 | 320 | 318 | 350 | 347 | 349 | 348 |
| Air flow rate (ml/min/g of catalyst) | | 0 | 11.1 | 29.8 | 50.6 | 0 | 9.92 | 30.74 | 51.31 |
| Oven temperature (° C.) | | 400 | 400 | 400 | 400 | 400 | 400 | 400 | 400 |
| Hot spot temperature (° C.) | | 412 | 416.3 | 408.58 | 407.6 | 411.9 | 408.2 | 406.1 | 405.4 |
| Yields in carbons ($TTU_c$ - %) | Acetaldehyde | 0.01 | 0 | 0.01 | 0.01 | 0 | 0.01 | 0 | 0 |
| | Propanol | 0 | 0 | 0 | 0 | 0 | 0 | 0 | 0 |
| | Acetone | 0.09 | 0.07 | 0.04 | 0.04 | 0.05 | 0.02 | 0 | 0 |
| | Acrolein | 0.01 | 0.02 | 0.02 | 0.02 | 0.02 | 0.02 | 0.02 | 0.03 |

TABLE 9-continued

| | | | | | | | | |
|---|---|---|---|---|---|---|---|---|
| Acetic acid | 0.95 | 0.95 | 0.36 | 0.31 | 0.58 | 0.28 | 0.03 | 0.01 |
| Propionic acid | 0.06 | 0.04 | 0.02 | 0.01 | 0.02 | 0.01 | 0 | 0 |
| Acrylic acid | 11.6 | 13.96 | 4.52 | 3.74 | 9.6 | 3.38 | 0.46 | 0.25 |
| CO | 1.38 | 2.01 | 0.74 | 0.55 | 1.43 | 0.71 | 0.16 | 0.15 |
| $CO_2$ | 1.11 | 1.55 | 0.58 | 0.45 | 1.07 | 0.72 | 0.29 | 0.26 |
| Propene | 4.13 | 4.01 | 3.09 | 2.37 | 3.53 | 2.2 | 1.15 | 0.81 |
| Propane | 79.68 | 79.55 | 90.66 | 92.42 | 83.91 | 91.87 | 97.9 | 96.39 |
| Oxygen | 55.56 | 52.91 | 83.65 | 83.97 | 66.54 | 85.12 | 97.03 | 97.68 |
| Carbon balance | 99 | 102.2 | 100.1 | 99.9 | 100.2 | 99.2 | 100 | 97.9 |
| Total carbon yield (TTG carbon) | 19.3 | 22.6 | 9.4 | 7.5 | 16.3 | 7.4 | 2.1 | 1.5 |
| Oxygen balance | 94.6 | 99.7 | 100.6 | 97.5 | 99.2 | 99.7 | 100.6 | 100.5 |
| Total oxygen yield ($TTG_m$) | 39 | 46.7 | 16.9 | 13.5 | 32.6 | 14.6 | 3.6 | 2.8 |
| Acidity measured (assay AB)* (ppm) | 4529.8 | 5960.5 | 2006.6 | 1552.6 | 3211.6 | 1364 | 210.1 | 89.1 |

*Assay A-B: acid-base assay of the number of moles of acid for soda

TABLE 10

| Catalyst | | D1 | D2 | D3 | D4 | A1 | A2 | A3 | A4 |
|---|---|---|---|---|---|---|---|---|---|
| Temperature of precalcination (° C.) | | 273 | 272 | 273 | 273 | 301 | 300 | 303 | 301 |
| Air flow rate (ml/min/g of catalyst) | | 0 | 1091 | 31.9 | 47.57 | 0 | 11 | 31.2 | 50.4 |
| Oven temperature (° C.) | | 400 | 400 | 400 | 400 | 400 | 400 | 400 | 400 |
| Hot spot temperature (° C.) | | 413.2 | 415.2 | 412.5 | 412.6 | 409 | 414.1 | 408.3 | 407.8 |
| Selectivities in carbon ($TTU_c$ - %) | Acetaldehyde | 0.04 | 0.04 | 0.03 | 0.04 | 0.04 | 0.04 | 0.13 | 0 |
| | Propanol | 0 | 0 | 0 | 0 | 0 | 0 | 0 | 0 |
| | Acetone | 0.55 | 0.2 | 0.27 | 0.29 | 0.58 | 0.33 | 0.49 | 0.34 |
| | Acrolein | 0.1 | 006 | 0.07 | 0.08 | 0.08 | 0.07 | 0.22 | 0.54 |
| | Acetic acid | 5.94 | 3.01 | 3.37 | 3.52 | 5.5 | 4.62 | 3.69 | 3.13 |
| | Propionic acid | 0.3 | 0.1 | 0.12 | 0.14 | 0.32 | 0.19 | 0.19 | 0.16 |
| | Acrylic acid | 47.5 | 59.8 | 61.8 | 61.8 | 53 | 60 | 48.5 | 35.6 |
| | CO | 8.53 | 12.1 | 9.83 | 9.54 | 7.84 | 9.23 | 7.32 | 6.01 |
| | $CO_2$ | 6.66 | 10.72 | 8.88 | 8.48 | 5.41 | 7.49 | 5.91 | 5.61 |
| | Propene | 30.33 | 13.95 | 15.6 | 16.09 | 27.28 | 18.04 | 33.57 | 48.57 |
| Catalyst | | B1 | B2 | B3 | B4 | C1 | C2 | C3 | C4 |
| Temperature of precalcination (° C.) | | 317 | 316 | 320 | 318 | 350 | 47 | 349 | 348 |
| Air flow rate (ml/min/g of catalyst) | | 0 | 11.1 | 29.8 | 50.6 | 0 | 9.92 | 30.74 | 51.31 |
| Oven temperature (° C.) | | 400 | 400 | 400 | 400 | 400 | 400 | 400 | 400 |
| Hot spot temperature (° C.) | | 412 | 416.3 | 408.58 | 407.6 | 411.9 | 408.2 | 406.1 | 405.4 |
| Selectivities in carbon ($TTU_c$ - %) | Acetaldehyde | 0 | 0.02 | 0.14 | 0.08 | 0.03 | 0.14 | 0 | 0 |
| | Propanol | 0 | 0 | 0 | 0 | 0 | 0 | 0 | 0 |
| | Acetone | 0.5 | 0.32 | 0.46 | 0.49 | 0.33 | 0.32 | 0 | 0 |
| | Acrolein | 0.1 | 0.07 | 0.22 | 0.23 | 0.13 | 0.32 | 1.03 | 2.09 |
| | Acetic acid | 4.9 | 4.21 | 3.87 | 4.09 | 3.57 | 3.81 | 1.34 | 0.87 |
| | Propionic acid | 0.28 | 0.19 | 0.17 | 0.19 | 0.14 | 0.11 | 0 | 0 |
| | Acrylic acid | 60 | 61.7 | 48.1 | 49.9 | 58.8 | 46 | 21.6 | 16.6 |
| | CO | 7.13 | 8.87 | 7.92 | 7.37 | 8.78 | 9.64 | 7.38 | 9.82 |
| | $CO_2$ | 5.73 | 6.85 | 6.19 | 5.95 | 6.56 | 9.78 | 13.77 | 17.2 |
| | Propene | 21.36 | 17.72 | 32.9 | 31.69 | 21.63 | 29.87 | 54.68 | 53.43 |

The conversion of the propane is generally considered as illustrating the catalyst activity: the greater this conversion, the more active the catalyst is. This conversion is given per TTG of carbon ($TTG_C = \Sigma\ TTU_C$).

It is noted that the conversion to propane is greater than 15% for the catalysts precalcined at 273° C. at flow rates of 10, 30 or 50 ml/min/g of catalyst, at 300° C. and 320° C. at low flow rates and at 350° C. at a no flow rate. It is also at these values that the highest acrylic acid yields (greater than 10%) and the greatest selectivities and the greatest acidities (greater than 3000 ppm) are obtained.

Generally, the TTG of oxygen ($TTG_{O_2}$) is also considered. As long as this TTG remains below 60%, it is considered that there is still enough oxygen which can serve to oxidize the propane. In this case, the maximum oxygen conversion capacities of the catalyst have not been achieved. The reaction temperature can be raised in order to improve the conversion to oxygen. However it is preferable to prevent the oxygen conversion from exceeding 80%.

The set of results relating to the selectivity and the yield of acetic acid is satisfactory.

It is thus noted that very good catalytic performances are obtained with several catalysts which have undergone very different precalcination conditions:

at 273° C. under flow rates of air of 10, 30 and 50 ml/min/g of catalyst;

at 300 and 320° C. under flow rates of air of 10 ml/min/g of catalyst; and

350° C. under no air flow rate.

Example 10

Preparation of a Catalyst E

Catalyst E was prepared with the formula: $MoV_{0.33}Te_{0.23}Nb_{0.11}Si_1O_x$ with the precursor: $MoV_{0.33}Te_{0.23}Nb_{0.11}Si_1(Oxalate)_{0.33}(NH_4)_{1.19}O_x$ in the manner given in Example 8 carrying out a precalcination at 319° C., under static air.

The drying which precedes the precalcination however has not been carried out in the oven but using microwaves.

Example 11

Comparison of Catalyst E and Catalyst B2

Catalysts B and B2 were tested at 6 different temperatures, from 380° C. to 430° C. The results obtained are recorded in Tables 11 and 12 below.

The yield of acrylic acid and the acidity are greater as the reaction temperature increases. These results show that the maximum yield of acrylic acid is reached at 420° C.

The invention claimed is:

1. Method for the production of acrylic acid from propane, in which a gaseous mixture comprising propane, molecular oxygen, water vapour, and optionally an inert gas is passed over a catalyst with the formula (I):

$$Mo_1V_aTe_bNb_cSi_dO_x \qquad (I)$$

in which:

a is between 0.006 and 1, inclusive;
b is between 0.006 and 1, inclusive;
c is between 0.006 and 1, inclusive;
d is between 0 and 3.5, inclusive; and
x is the quantity of oxygen bound to the other elements and depends on their oxidation state,

TABLE 11

|  |  | E |  |  |  |  | B2 |  |  |  |  |
|---|---|---|---|---|---|---|---|---|---|---|---|
| Temperature of precalcination (° C.) |  | 319 |  |  |  |  | 316 |  |  |  |  |
| Air flow rate (ml/min/g) catalyst |  | 0 |  |  |  |  | 0 |  |  |  |  |
| Oven temperature (° C.) |  | 380 | 400 | 410 | 420 | 430 | 380 | 400 | 410 | 420 | 430 |
| Hot spot temperature (° C.) |  | 389.6 | 414.3 | 426.8 | 439.9 | 452.2 | 391.3 | 416.3 | 429.3 | 443 | 459.1 |
| Yields in carbon TTU$_c$ in %) | Acetaldehyde | 0 | 0 | 0 | 0.01 | 0.71 | 0 | 0 | 0 | 0 | 0.48 |
|  | Propanol | 0 | 0 | 0 | 0 | 0.01 | 0 | 0 | 0 | 0 | 0 |
|  | Acetone | 0.12 | 0.06 | 0.04 | 0.03 | 0.12 | 0.14 | 0.07 | 0.06 | 0.04 | 0.12 |
|  | Acrolein | 0.01 | 0.01 | 0.02 | 0.02 | 0.03 | 0.01 | 0.02 | 0.02 | 0.02 | 0.03 |
|  | Acetic acid | 0.71 | 0.86 | 0.79 | 0.74 | 3.23 | 0.88 | 0.95 | 0.94 | 0.95 | 3.08 |
|  | Propionic acid | 0.08 | 0.04 | 0.03 | 0.02 | 2.95 | 0.09 | 0.04 | 0.03 | 0.02 | 0.96 |
|  | Acrylic acid | 9.88 | 16.1 | 18.7 | 20.87 | 6.63 | 9.52 | 13.96 | 17 | 19.19 | 9.75 |
|  | CO | 0.82 | 1.71 | 2.6 | 3.98 | 6.76 | 0.98 | 2.01 | 3.09 | 4.8 | 7.26 |
|  | $CO_2$ | 0.49 | 1.4 | 2.39 | 3.99 | 8.92 | 0.63 | 1.55 | 2.68 | 4.38 | 8.2 |
|  | Propene | 3.66 | 3.94 | 3.79 | 3.77 | 3.8 | 3.74 | 4.01 | 3.96 | 3.86 | 4.12 |
|  | Propane | 85.4 | 78.88 | 71.62 | 68.55 | 65.74 | 86.1 | 79.55 | 73.41 | 68.38 | 66.67 |
| Oxygen |  | 71.14 | 48.49 | 34.54 | 18.77 | 0.04 | 71.44 | 52.91 | 35.6 | 17.2 | 0.27 |
| Carbon balance |  | 101.2 | 103 | 100 | 102 | 98.9 | 102.1 | 102.2 | 101.2 | 101.6 | 100.7 |
| Total carbon yield (TTG) |  | 15.8 | 24.1 | 28.4 | 33.4 | 33.1 | 16 | 22.6 | 27.8 | 33.3 | 34 |
| Oxygen balance |  | 99.7 | 97.5 | 96.6 | 97.8 | 95.3 | 101 | 99.7 | 97.8 | 98.2 | 96.6 |
| Total oxygen yield (TTG) |  | 28.6 | 49 | 62 | 79.1 | 95.3 | 29.5 | 46.7 | 62.2 | 81 | 96.3 |
| Acidity measured (assay AB) (ppm) |  | 4216.7 | 6522.8 | 7207.2 | 0136 | 5580.5 | 3828.5 | 5960.5 | 6906.7 | 8610.2 | 5790.5 |

TABLE 12

|  |  | E |  |  |  |  | B2 |  |  |  |  |
|---|---|---|---|---|---|---|---|---|---|---|---|
| Temperature of precalcination (° C.) |  | 319 |  |  |  |  | 316 |  |  |  |  |
| Air flow rate (ml/min/g) catalyst |  | 0 |  |  |  |  | 11.1 |  |  |  |  |
| Oven temperature (° C.) |  | 380 | 400 | 410 | 420 | 430 | 380 | 400 | 410 | 420 | 430 |
| Hot spot temperature (° C.) |  | 389.6 | 414.3 | 426.8 | 439.9 | 452.2 | 391.3 | 416.3 | 429.3 | 443 | 459.1 |
| Yields in carbon TTU$_c$ in %) | Acetaldehyde | 0 | 0 | 0 | 0 | 2.13 | 0 | 0.02 | 0 | 0 | 1.41 |
|  | Propanol | 0 | 0 | 0 | 0 | 0.03 | 0 | 0 | 0 | 0 | 0 |
|  | Acetone | 0.8 | 0.26 | 0.2 | 0.1 | 0.35 | 0.9 | 0.32 | 0.2 | 0.1 | 0.35 |
|  | Acrolein | 0.1 | 0.05 | 0.1 | 0.1 | 0.08 | 0.1 | 0.07 | 0.1 | 0.1 | 0.08 |
|  | Acetic acid | 4.5 | 3.57 | 2.8 | 2.2 | 9.75 | 5.5 | 4.21 | 3.4 | 2.9 | 9.05 |
|  | Propionic acid | 0.5 | 0.18 | 0.1 | 0.06 | 8.89 | 0.5 | 0.19 | 0.1 | 0.06 | 2.83 |
|  | Acrylic acid | 62.6 | 66.7 | 65.9 | 62.4 | 20 | 59.6 | 61.7 | 61.2 | 57.7 | 28.7 |
|  | CO | 5.17 | 7.08 | 9.17 | 11.9 | 20.4 | 6.14 | 8.87 | 11.11 | 14.43 | 21.36 |
|  | $CO_2$ | 3.12 | 5.8 | 8.44 | 11.94 | 26.91 | 3.94 | 6.85 | 9.65 | 13.17 | 24.11 |
|  | Propene | 23.2 | 16.34 | 13.37 | 11.28 | 11.46 | 23.37 | 17.72 | 14.26 | 11.6 | 12.13 |

It is noted that the behaviours are similar for these two catalysts. Therefore there is no difference a priori between drying with microwaves and drying in the oven.

in order to oxidize the propane to acrylic acid, wherein the molar ratio propane/molecular oxygen in the initial gaseous mixture is greater than or equal to 0.5.

2. Method according to claim 1, in which the molar proportions of the constituents of the initial gaseous mixture are as follows:

propane/O$_2$/inert gas/H$_2$O (vapour)=1/0.05-2/1-10/1-10.

3. Method according to claim 1, in which the molar proportions of the constituents of the initial gaseous mixture are as follows:

propane/O$_2$/inert gas/H$_2$O (vapour)=1/0.1-1/1-5/1-5.

4. Method according to claim 1, in which, in the catalyst of formula (I):
a is between 0.09 and 0.8, inclusive;
b is between 0.04 and 0.6, inclusive;
c is between 0.01 and 0.4, inclusive; and
d is between 0.4 and 1.6, inclusive.

5. Method according to claim 1, wherein the oxidation reactions are carried out at a temperature of 200 to 500° C.

6. Method according to claim 1, wherein the oxidation reactions are carried out at a temperature of 250 to 450° C.

7. Method according to claim 1, wherein the oxidation reactions are carried out at a pressure of 1.01×10$^4$ to 1.01×10$^6$ Pa (0.1 to 10 atmospheres).

8. Method according to claim 1, wherein the oxidation reactions are carried out at a pressure of 5.05×10$^4$ to 5.05×10$^5$ Pa (0.5-5 atmospheres).

9. Method according to claim 1, which is used until there is a reduction ratio of the catalyst comprised between 0.1 and 10 g of oxygen per kg of catalyst.

10. Method according to claim 1, wherein once the catalyst has at least partially changed to the reduced state, its regeneration is carried out according to reaction (3):

$$\text{SOLID}_{reduced} + O_2 \rightarrow \text{SOLID}_{oxidized} \quad (3)$$

by heating in the presence of oxygen or a gas containing oxygen at a temperature of 250 to 500° C., for a period necessary for the reoxidation of the catalyst.

11. Method according to claim 10, wherein the oxidation and the regeneration (3) reactions are carried out in a device with two stages, namely a reactor and a regenerator which operate simultaneously and in which two catalyst loads alternate periodically.

12. Method according to claim 10, wherein the oxidation and the regeneration (3) reactions are carried out in the same reactor alternating the periods of reaction and regeneration.

13. Method according to claim 10, wherein the oxidation and the regeneration (3) reactions are carried out in a reactor with a moving bed.

14. Method according to claim 1, in which:
a) the initial gaseous mixture is introduced into a first reactor with a moving catalyst bed,
b) at outlet of the first reactor, the gaseous mixture is separated from the catalyst;
c) the catalyst is returned into a regenerator;
d) the gaseous mixture is introduced into a second reactor with a moving catalyst bed;
e) at outlet of the second reactor, the gaseous mixture is separated from the catalyst and acrylic acid contained in the separated gaseous mixture is recovered;
f) the catalyst is returned into the regenerator; and
g) regenerated catalyst from the regenerator is reintroduced into the first and second reactors.

15. Method according to claim 14, in which the first and second reactors are vertical and the catalyst is moved upwards by the gas flow.

16. Method according to claim 1, wherein the oxidation reactions are carried out with a residence time of 0.01 to 90 seconds in each reactor.

17. Method according to claim 1, wherein the oxidation reactions are carried out with a residence time of 0.1 to 30 seconds in each reactor.

18. Method according to claim 1, wherein propylene produced or the propane which has not reacted or both are recycled to an inlet of a reactor, or if there are several reactors, to inlet of a first reactor.

19. Method according to claim 1, in which a reactor, or when there are several reactors, at least one of the reactors, also comprises a cocatalyst corresponding to the following formula (II):

$$Mo_1Bi_{a'}Fe_{b'}Co_{c'}Ni_{d'}K_{e'}Sb_{f'}Ti_{g'}Si_{h'}Ca_{i'}Nb_{j'}Te_{k'}Pb_{l'}W_{m'}Cu_{n'} \quad (II)$$

in which:
a' is between 0.006 and 1, inclusive
b' is between 0 and 3.5, inclusive;
c' is between 0 and 3.5, inclusive;
d' is between 0 and 3.5, inclusive;
e' is between 0 and 1, inclusive;
f' is between 0 and 1, inclusive;
g' is between 0 and 1, inclusive;
h' is between 0 and 3.5, inclusive;
i' is between 0 and 1, inclusive;
j' is between 0 and 1, inclusive;
k' is between 0 and 1, inclusive;
l' is between 0 and 1, inclusive;
m' is between 0 and 1, inclusive; and
n' is between 0 and 1, inclusive.

20. Method according to claim 19, in which the cocatalyst is regenerated and circulates, in the same way as the catalyst.

21. Method according to claim 19, in which, in the cocatalyst of formula (II):
a' is between 0.01 and 0.4, inclusive;
b' is between 0.2 and 1.6, inclusive;
c' is between 0.3 and 1.6, inclusive;
d' is between 0.1 and 0.6, inclusive;
e' is between 0.006 and 0.01, inclusive;
f' is between 0 and 0.4, inclusive;
g' is between 0 and 0.4, inclusive;
h' is between 0.01 and 1.6, inclusive
i' is between 0 and 0.4, inclusive;
j' is between 0 and 0.4, inclusive;
k' is between 0 and 0.4, inclusive;
l' is between 0 and 0.4, inclusive;
m' is between 0 and 0.4, inclusive; and
n' is between 0 and 0.4, inclusive.

22. Method according to claim 19, in which, a weight ratio of the catalyst to the cocatalyst greater than 0.5 is used.

23. Method according to claim 19, in which, a weight ratio of the catalyst to the cocatalyst of at least 1 is used.

24. Method according to claim 19, in which the catalyst and the cocatalyst are mixed.

25. Method according to claim 19, in which the catalyst and the cocatalyst are present in the form of pellets, each pellet comprising both the catalyst and the cocatalyst.

26. Method according to claim 1, comprising repetition, in a reactor provided with the catalyst of formula (I) defined in claim 1, or the cocatalyst of formula (II) defined in claim 19, of a cycle comprising the following successive stages:
1) a stage of injection of the gaseous mixture as defined in claim 1;
2) a stage of injection of water vapour or inert gas;

3) a stage of injection of a mixture of molecular oxygen, water vapour or inert gas; and 4) a stage of injection of water vapour or inert gas.

27. Method according to claim 26, wherein the cycle comprises an additional stage which precedes or follows stage 1) and during which a gaseous mixture corresponding to that of stage 1) but without molecular oxygen is injected, the molar ratio propane/molecular oxygen then being calculated globally for stage 1) and this additional stage.

28. Method according to claim 27, wherein the additional stage precedes stage I) in the cycle.

29. Method according to claim 27, wherein the reactor is a reactor with a moving bed.

30. Method for the production of acrylic acid from propane, in which a gaseous mixture comprising propane, molecular oxygen, water vapour, and optionally an inert gas is passed over a catalyst with the formula (I):

$$Mo_1V_aTe_bNb_cSi_dO_x \tag{I}$$

in which:
a is between 0.006 and 1, inclusive;
b is between 0.006 and 1, inclusive;
c is between 0.006 and 1, inclusive;
d is between 0 and 3.5, inclusive; and
x is the quantity of oxygen bound to the other elements and depends on their oxidation state, in order to oxidize the propane to acrylic acid, wherein the molar ratio propane/molecular oxygen in the initial gaseous mixture is greater than or equal to 0.5, and in which a) the initial gaseous mixture is introduced into a first reactor with a moving catalyst bed, b) at the outlet of the first reactor, the gases are separated from the catalyst;

c) the catalyst is returned into a regenerator;

d) the gases are introduced into a second reactor with a moving catalyst bed;

e) at the outlet of the second reactor, the gases are separated from the catalyst and the acrylic acid contained in the separated gases is recovered;

f) the catalyst is returned into the regenerator; and g) the regenerated catalyst from the regenerator is reintroduced into the first and second reactors.

31. Method according to claim 30, in which the molar proportions of the constituents of the initial gaseous mixture are as follows:

propane/O$_2$/inert gas/H$_2$O (vapour)=1/0.05-2/1-10/1-10.

32. Method according to claim 30, in which, in the catalyst of formula (I):
a is between 0.09 and 0.8, inclusive;
b is between 0.04 and 0.6, inclusive;
c is between 0.01 and 0.4, inclusive; and
d is between 0.4 and 1.6, inclusive.

33. Method for the production of acrylic acid from propane, in which a gaseous mixture comprising propane, molecular oxygen, water vapour, and optionally an inert gas is passed over a catalyst with formula (I):

$$Mo_1V_aTe_bNb_cSi_dO_x \tag{I}$$

in which:
a is between 0.006 and 1, inclusive;
b is between 0.006 and 1, inclusive;
c is between 0.006 and 1, inclusive;
d is between 0 and 3.5, inclusive; and
x is the quantity of oxygen bound to the other elements and depends on their oxidation state, in order to oxidize the propane to acrylic acid, wherein the molar ratio propane/molecular oxygen in the initial gaseous mixture is greater than or equal to 0.5, comprising repetition, in a reactor provided with the catalyst of formula (I) defined above, of a cycle comprising the following successive stages:

1) a stage of injection of the gaseous mixture as defined above;

2) a stage of injection of water vapour or inert gas;

3) a stage of injection of a mixture of molecular oxygen, water vapour or inert gas; and 4) a stage of injection of water vapour or inert gas.

34. Method according to claim 33, in which, in the catalyst of formula (I):
a is between 0.09 and 0.8, inclusive;
b is between 0.04 and 0.6, inclusive;
c is between 0.01 and 0.4, inclusive; and
d is between 0.4 and 1.6, inclusive.

35. Method according to claim 33, wherein the cycle comprises an additional stage which precedes or follows stage 1) and during which a gaseous mixture corresponding to that of stage 1) but without molecular oxygen is injected, the molar ratio propane/molecular oxygen then being calculated globally for stage 1) and this additional stage.

36. Method according to claim 35, wherein the additional stage precedes stage I) in the cycle.

* * * * *